(12) United States Patent
Eng et al.

(10) Patent No.: US 12,121,620 B2
(45) Date of Patent: Oct. 22, 2024

(54) METHOD AND SYSTEM FOR MASK DISINFECTION

(71) Applicant: The University of Chicago, Chicago, IL (US)

(72) Inventors: Peter Eng, Chicago, IL (US); Patrick J. La Riviere, Chicago, IL (US); Jon Brickman, Rolling Meadows, IL (US); Naoum Issa, Chicago, IL (US); Talon Chandler, Chicago, IL (US); Michael Proskey, Aurora, IL (US); Joanne E. Stubbs, Chicago, IL (US)

(73) Assignee: THE UNIVERSITY OF CHICAGO, Chicago, IL (US)

(*) Notice: Subject to any disclaimer, the term of this patent is extended or adjusted under 35 U.S.C. 154(b) by 733 days.

(21) Appl. No.: 17/326,860

(22) Filed: May 21, 2021

(65) Prior Publication Data
US 2021/0361798 A1  Nov. 25, 2021

Related U.S. Application Data

(60) Provisional application No. 63/028,713, filed on May 22, 2020.

(51) Int. Cl.
*A61L 2/10* (2006.01)
*A61L 2/24* (2006.01)

(52) U.S. Cl.
CPC .............. *A61L 2/10* (2013.01); *A61L 2/24* (2013.01); *A61L 2202/11* (2013.01); *A61L 2202/122* (2013.01); *A61L 2202/14* (2013.01); *A61L 2202/26* (2013.01)

(58) Field of Classification Search
CPC .......... A61L 2/10; A61L 2/24; A61L 2202/11; A61L 2202/14; A61L 2202/26; A61L 2202/122
See application file for complete search history.

(56) References Cited

U.S. PATENT DOCUMENTS 10,842,896 B1 * 11/2020 Mehra .................. G06Q 20/027

OTHER PUBLICATIONS

Mills, D., Harnish, D., Lawrence, C., Sandoval-Powers, M., Heimbuch, B., "Ultraviolet germicidal irradiation of influenza-contaminated N95 filtering facepiece respirators," *American Journal of Infection Control* 2018, 46(7), E49-E55.

(Continued)

*Primary Examiner* — Sean E Conley
(74) *Attorney, Agent, or Firm* — Bell & Manning, LLC

(57) ABSTRACT

A disinfection system includes a mask chamber and a cassette trolley rail mounted to the mask chamber. The system also includes a mask cassette configured to hold one or more masks and configured to mount to the cassette trolley rail such that the mask cassette translates along the cassette trolley rail. The system also includes a first array of lamps mounted to a first lamp mount within the mask chamber, where the first array of lamps is positioned to emit radiation toward a first side of the mask cassette. The system further includes a second array of lamps mounted to a second lamp mount within the mask chamber, where the second array of lamps is positioned to emit radiation toward a second side of the mask cassette that is opposite the first side of the mask cassette.

16 Claims, 23 Drawing Sheets

(56) References Cited

OTHER PUBLICATIONS

Lindsley, W., Martin, S., Thewlis, R., Sarkisian, K., Nwoko, J., Mead, K., Noti, J., "Effects of Ultraviolet Germicidal Irradiation (UVGI) on N95 Respirator Filtration Performance and Structural Integrity," *Journal of Occupational and Environmental Hygiene* 2015, 12(8), 509-517.

Bergman, M. S., Viscusi, D. J., Zhuang, Z., Palmiero, A. J., Powell, J. B., & Shaffer, R. E. (2012). "Impact of multiple consecutive donnings on filtering facepiece respirator fit," *American Journal of Infection Control*, 40(4), 375-380.

Wladyslaw Kowalski, "Ultraviolet Germicidal Irradiation Handbook: UVGI for Air and Surface Disinfection," Springer Heidelberg Dordrecht London New York; DOI 10.1007/978-3-642-01999-9.

N95 Decon Review Team. Technical Report for UV-C-Based N95 Reuse Risk Management. N95decon.org. Version 1.2, Apr. 1, 2020; pp. 1-8.

Heimbuch, B., Harnish, D., "Research to Mitigate a Shortage of Respiratory Protection Devices During Public Health Emergencies," *Applied Research Associates, Inc.*, Report No. HHSF223201400158C to FDA: 2019.

Orbitform Medical UVC Decontamination Chamber (UVC DC), Datasheet [online]. Orbitform Medical, LLC, 2020. [retrieved on Sep. 8, 2021]. Retrieved from Internet: <URL: www.orbitformmedical.com/uvc-decontamination-chamber>.

Cleanbox, Datasheet [online]. Cleanbox Headquarters. [retrieved on Sep. 8, 2021]. Retrieved from Internet: < URL: www.cleanboxtech.com>.

\* cited by examiner

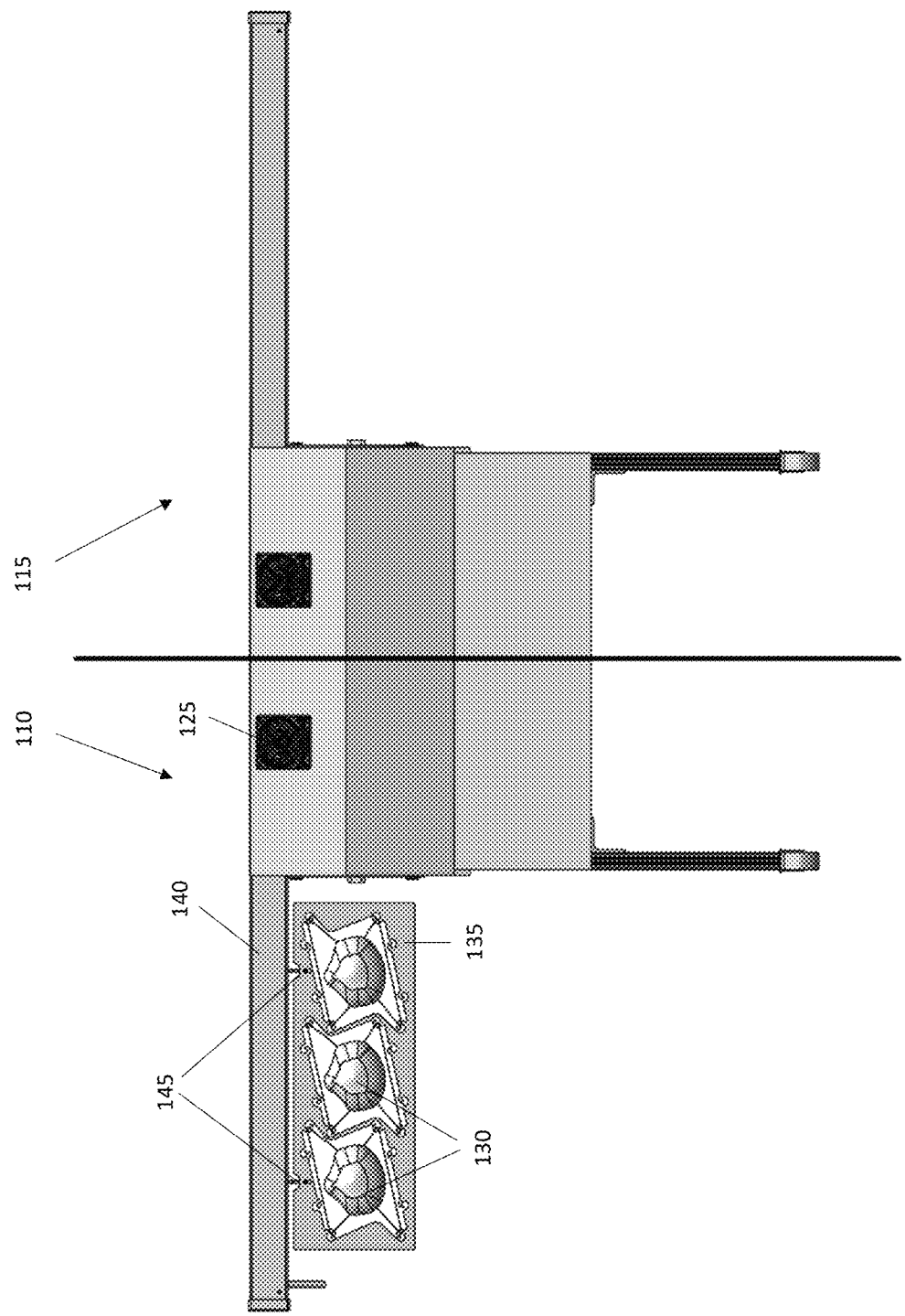

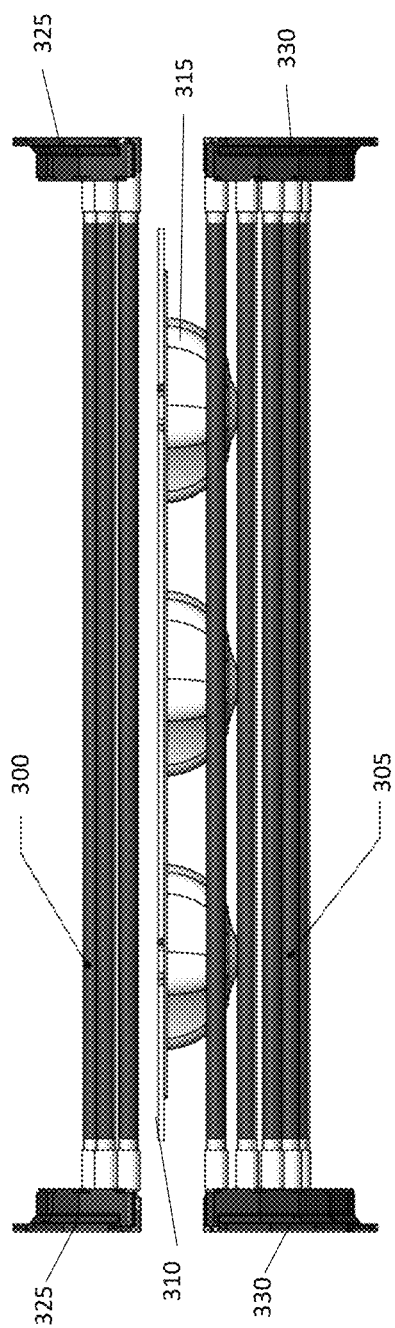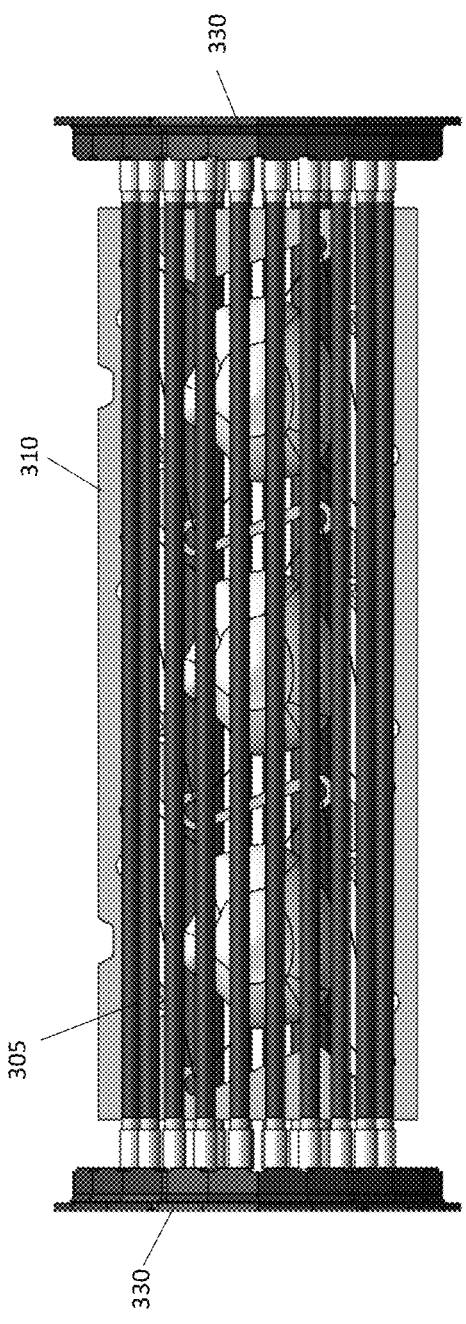
Fig. 3A
Fig. 3B

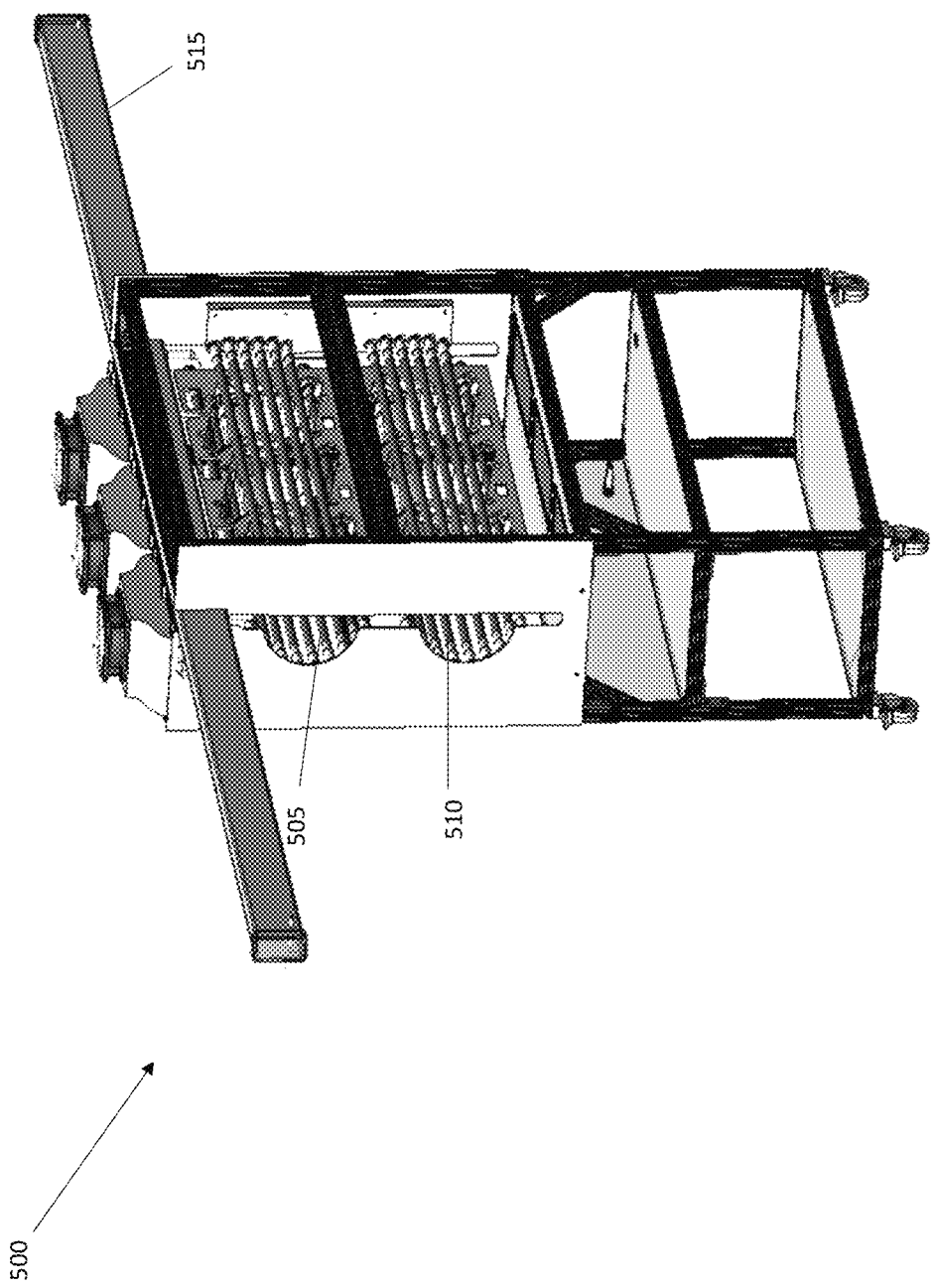

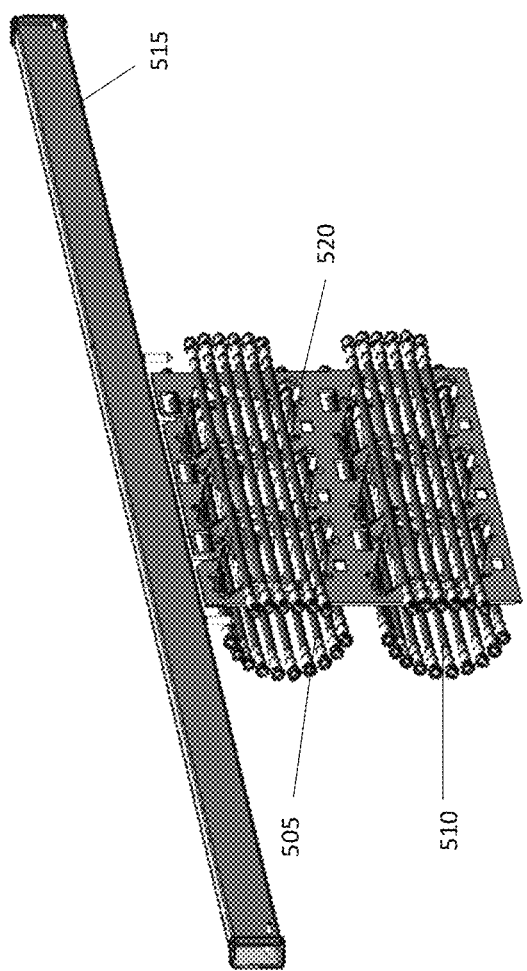

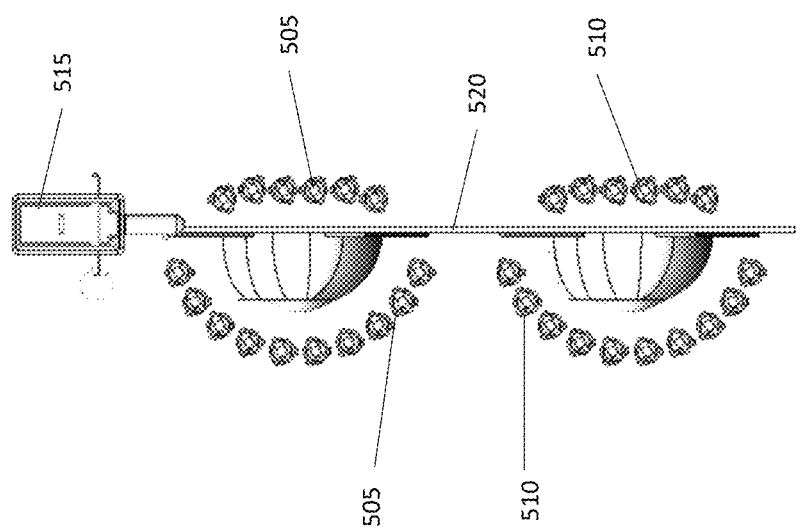

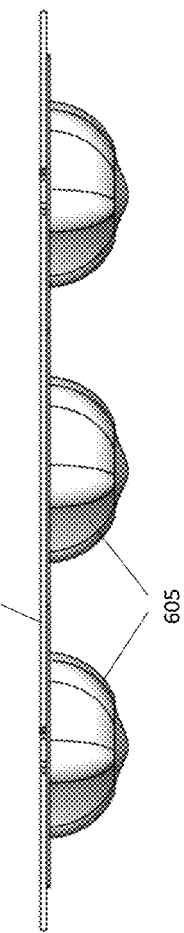
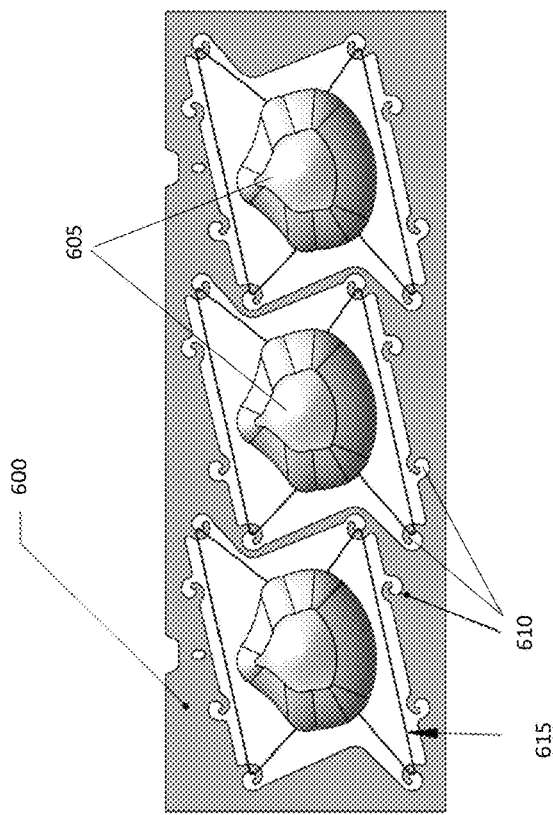
Fig. 6B
Fig. 6A

| Sensor Location Lower | Mask [mW/cm²] | |
|---|---|---|
| | End | Center |
| Side looking out | 27 | 40 |
| Looking down | 37 | 41.7 |
| Looking up | 46 | 47.7 |
| Looking in | 41.5 | 37.5 |
| Looking front | 44.5 | 46.6 |
| Inside looking back | 31 | 31.5 |
| Inside looking out | 31.6 | 34.2 |
| Inside looking down | 31.2 | 32 |
| Inside looking up | 32.4 | 33.8 |
| Inside looking in | 35.5 | 36.4 |

Fig. 8

METHOD AND SYSTEM FOR MASK DISINFECTION

CROSS-REFERENCE TO RELATED APPLICATION

The present application claims the priority benefit of U.S. Provisional Patent App. No. 63/028,713 filed on May 22, 2020, the entire disclosure of which is incorporated by reference herein.

BACKGROUND

The COVID-19 pandemic has caused a significant increase in demand for personal protective equipment and supplies for both the medical community and personal use. For example, it is recommended that all individuals wear face masks when they are out in certain public settings to help avoid transmission of the disease. As a result, the United States and many countries throughout the world are experiencing severe shortages of face masks and respirators.

SUMMARY

An illustrative disinfection system includes a mask chamber and a cassette trolley rail mounted to the mask chamber. The system also includes a mask cassette configured to hold one or more masks and configured to mount to the cassette trolley rail such that the mask cassette translates along the cassette trolley rail. The system also includes a first array of lamps mounted to a first lamp mount within the mask chamber, where the first array of lamps is positioned to emit radiation toward a first side of the mask cassette. The system further includes a second array of lamps mounted to a second lamp mount within the mask chamber, where the second array of lamps is positioned to emit radiation toward a second side of the mask cassette that is opposite the first side of the mask cassette.

In some embodiments, the cassette trolley rail includes a first portion that extends outside of the mask chamber at a used mask end of the mask chamber, a second portion that extends within the mask chamber, and a third portion that extends outside of the mask chamber at a clean mask end of the mask chamber. In some embodiments, the system includes a first cabinet positioned at the used mask end of the mask chamber and configured to house the first portion of the cassette trolley rail. The system may also include a second cabinet positioned at the clean mask end of the mask chamber and configured to house the third portion of the cassette trolley rail.

In some embodiments, the first lamp mount has a first radius of curvature and the second lamp mount has a second radius of curvature that is different than the first radius of curvature. In some embodiments, the first array of lamps includes six lamps and the second array of lamps includes ten lamps. In other embodiments, the mask cassette includes a plurality of openings configured to accommodate a corresponding plurality of masks. Each of the plurality of openings can include a plurality of hooks configured to hold straps of the plurality of masks.

In some embodiments, the system includes a fan mounted to an opening in the mask chamber to provide air flow over the first array of lamps and the second array of lamps, and a filter mounted over the opening. The system may also include one or more hooks extending from the cassette trolley rail and configured to hold the mask cassette, where the one or more hooks are exposed to one or more of the first array of lamps and the second array of lamps during use of the system. In some embodiments, the system includes a thermocouple within the mask chamber to monitor an internal temperature of the mask chamber, and the first array of lamps and the second array of lamps are configured (e.g., processor controlled) to turn off if the internal temperature detected by the thermocouple exceeds a threshold value.

The system may also include an irradiance sensor mounted within the mask chamber and configured to monitor the first array of lamps and the second array of lamps during a disinfection operation to ensure that all of the lamps are functional. The irradiance sensor, processor, or other system component can generate an alert if it is determined that any of the lamps is not functional during the disinfection operation. In other embodiments, each lamp extends along the same direction as the cassette trolley rail, and each lamp is longer than a distance between most distant masks on a filled mask cassette.

An illustrative method of disinfecting masks includes loading a mask cassette with a plurality of masks. The method also includes placing the mask cassette with the plurality of masks into a mask chamber. The method also includes activating a first array of lamps and a second array of lamps within the mask chamber. The first array of lamps is positioned to emit radiation toward a first side of the mask cassette and the second array of lamps is positioned to emit radiation toward a second side of the mask cassette that is opposite the first side of the mask cassette. In some embodiments, the method also includes mounting the mask cassette with the plurality of masks to a cassette trolley rail that extends into the mask chamber. In some embodiments, the method includes detecting, by an irradiance sensor mounted within the mask chamber, that one or more lamps in the first array of lamps or the second array of lamps is non-functional. In other embodiments, the method can include generating an alert (e.g., by the sensor or a processor coupled to the sensor) responsive to the detection of the one or more lamps that is non-functional.

Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings.

FIG. 1C is a front view of the mask disinfection system in accordance with an illustrative embodiment.

FIG. 3A is a top view of a first lamp array and a second lamp array with a mask cassette and masks positioned between the lamp arrays in accordance with an illustrative embodiment.

FIG. 3B is a side view of the lamp arrays in accordance with an illustrative embodiment.

FIG. 5A is a first perspective view of a disinfection system with the mask chamber walls removed in accordance with another illustrative embodiment.

FIG. 5C is a perspective view of the lamp arrays, cassette trolley rail 515, and loaded mask cassette 520 in accordance with an illustrative embodiment.

FIG. 5D is an end view of the vertically stacked double set of lamp arrays in accordance with an illustrative embodiment.

FIG. 6A is a side view of a mask cassette loaded with masks in accordance with an illustrative embodiment.

FIG. 6B is a top view of the mask cassette loaded with masks in accordance with an illustrative embodiment.

FIG. 8 depicts a table that shows the results of measurements for the mask in the center of the array (Center) and a mask on the edge of the array (End) in accordance with an illustrative embodiment.

DETAILED DESCRIPTION

One way to help combat the attendant scarcity of medical personal protective equipment (PPE) that has resulted from the COVID-19 pandemic is to develop strategies for reusing and extending the lives of equipment such as N95 respirators. Described herein are disinfection systems to extend the lives of such respirators and other face masks. The design parameters for the proposed disinfection system are based on studies examining the effectiveness of ultra-violet germicidal irradiation (UVGI) for disinfecting N95 masks inoculated with H1N1 influenza virus. It has been determined that a dose of 1 Joule/square centimeter ($J/cm^2$) with a wavelength of 254 nanometers (nm) results in a 3-4 log 10 reduction of initial viral load, with final concentrations of viable virus below detection limits. Alternatively, a different wavelength of radiation can be used. It was further determined that masks can be disinfected dozens of times without loss of filtration efficiency or reduction in material strength.

Current UVGI systems have a low throughput, do not separate contaminated and decontaminated workspaces, and/or suffer from shadowing that prevents decontamination of all respirator surfaces. To address this issue, the inventors have developed a UV lamp arrangement that optimizes irradiation of all mask surfaces. This lamp arrangement is placed into a mask chamber that separates contaminated and decontaminated workspaces, protecting workers as well as maintaining decontamination after processing.

Figure 1A:
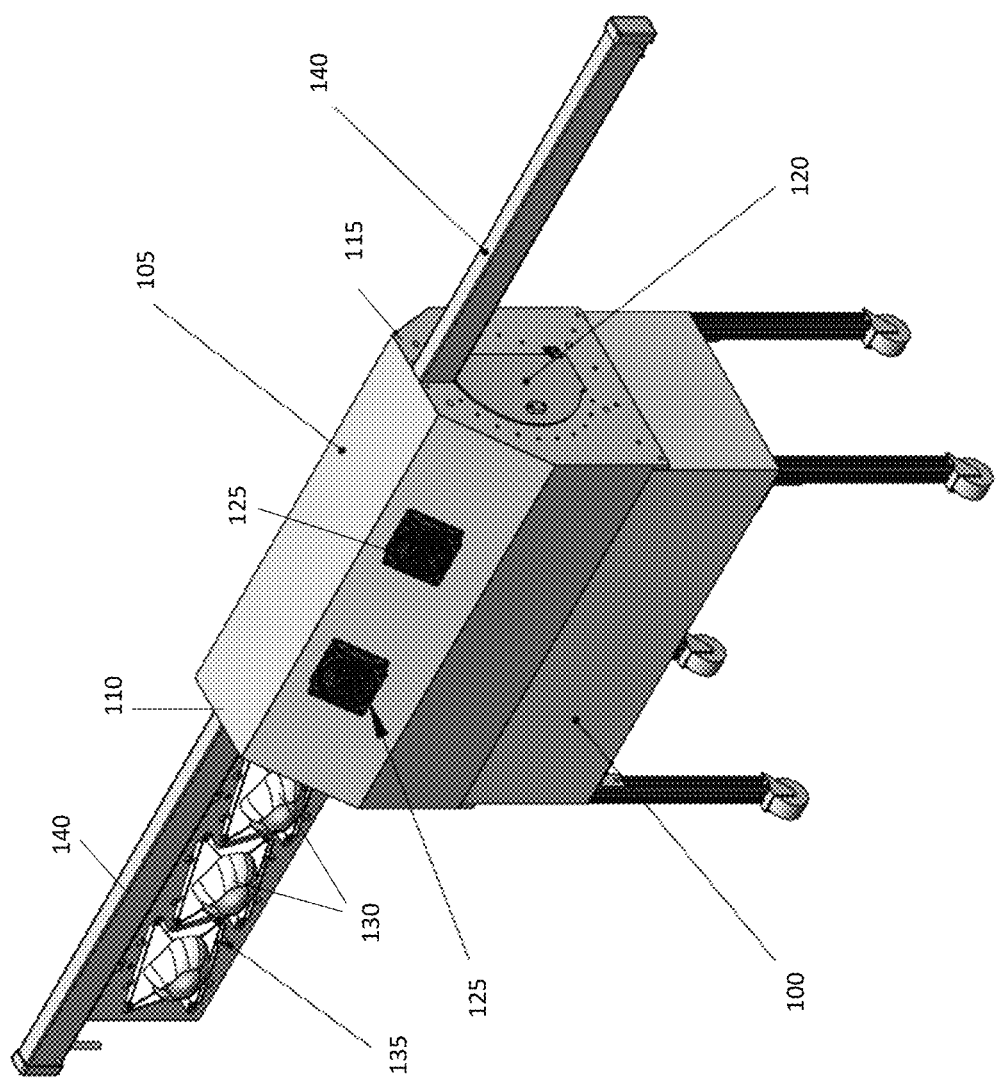
FIG. 1A is a perspective view of a mask disinfection system in accordance with an illustrative embodiment.
Figure 1B:
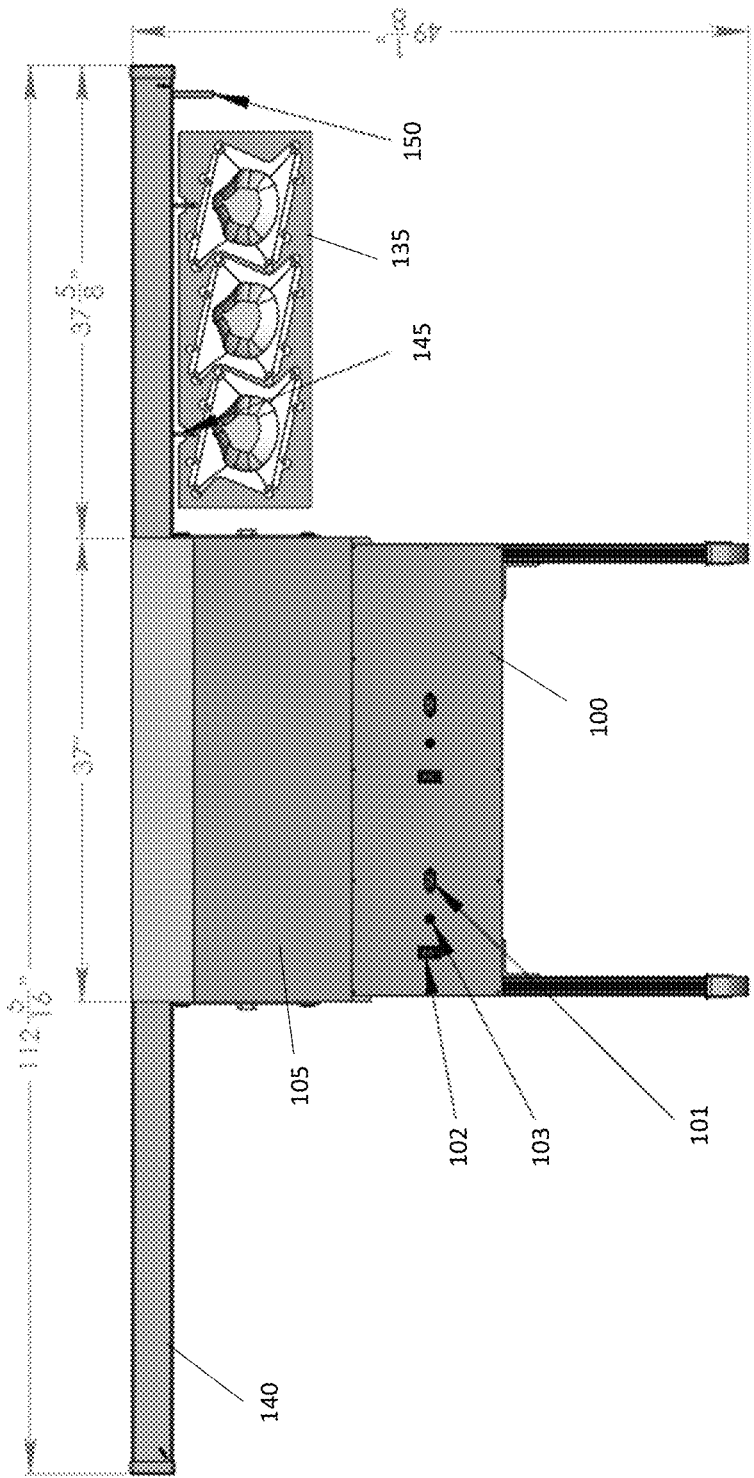
FIG. 1B is a rear view of the mask disinfection system in accordance with an illustrative embodiment.

FIG. 1A is a perspective view of a mask disinfection system in accordance with an illustrative embodiment. FIG. 1B is a rear view of the mask disinfection system in accordance with an illustrative embodiment. FIG. 1C is a front view of the mask disinfection system in accordance with an illustrative embodiment. It is noted that depicted dimensions in the figures are merely illustrative, and components having different dimensions can be used in alternative embodiments. Similarly, different types of components may also be used in alternative embodiments.

As shown, the system includes a power cabinet 100 that is designed to house a power input 101 for a mask chamber 105, a power input 102 for the lamps, one or more fuses 103 for the system, wiring, other electronics, etc. In an illustrative embodiment, the power cabinet 100 receives power from a power source such as a wall outlet. Alternatively, the power cabinet 100 may include a battery bank and/or other power source such that the system can be portable. Mounted to the power cabinet 100 is the mask chamber (or decontamination cabinet) 105, which is a sealed chamber that houses the lamps. The mask chamber 105 includes a used mask side 110 and a clean mask side 115. Used masks enter the mask chamber through a door positioned on the used mask side of the chamber, and clean masks exit the mask chamber through a door 120 positioned on the clean mask side 115 of the mask chamber 105. The mask chamber 105 also includes openings with fans 125 mounted therein to provide cooling air flow within the mask chamber 105. The openings in the mask chamber can also include filters (e.g., high efficiency particulate air (HEPA) filters) to seal the mask chamber 105 from the external environment and prevent the dissemination of airborne particles from within the mask chamber 105.

Used masks 130 are mounted to a cassette 135, which in turn is mounted to a cassette trolley rail 140 via one or more hooks 145 extending down from the rail 140. In an illustrative embodiment, the cassette trolley rail can include a hollow outer frame with a slot at the bottom. Positioned within the outer frame is a cassette mount that is shorter in length than the outer frame and designed to slide within the outer frame on wheels or bearings. The hooks 145 extend down from the cassette mount through the slot in the outer frame, and are used to mount the cassette 135 such that it is able to translate along the cassette trolley rail 140. Additionally, one or more handles 150 can also extend down through the slot in the outer frame. The one or more handles 150 can be used to manually move the cassette mount (and attached cassette) along the cassette trolley rail 140.

The cassette trolley rail 140 has a first portion that extends from the used mask side of the mask chamber, a second portion that is within the mask chamber, and a third portion that extends from the clean mask side of the mask chamber. As discussed above, the cassette 135 is mounted such that it slides along the cassette trolley rail 140. As such, the cassette 135 loaded with used masks 130 can be slid from the first portion of the cassette trolley rail 140 (on the used mask side) to the second portion of the cassette trolley (i.e., into the mask chamber for disinfection), and then onto the third portion of the cassette trolley (on the clean mask side). In one embodiment, a user can manually move the cassette 135 of masks into the mask chamber 105 and remove it therefrom using the handle(s) 150 mounted to the cassette trolley rail 140. In an alternative embodiment, the cassette 135 can be moved automatically into and through the mask chamber 105 using a chain/gear drive assembly, or any other drive system.

In another embodiment, a first cabinet with interlocking doors can be positioned on the used mask side of the cabinet and configured to receive one or more mask cassettes loaded with masks to be disinfected. Similarly, the clean mask side of the system can include a second cabinet with interlocking doors, where the second cabinet is designed to receive the one or more mask cassettes after disinfection. Use of such cabinets ensures that the UV radiation used to disinfect does not escape the system and cause harm to operators. This allows operators to use the system without UV protective gear.

Figure 2A:
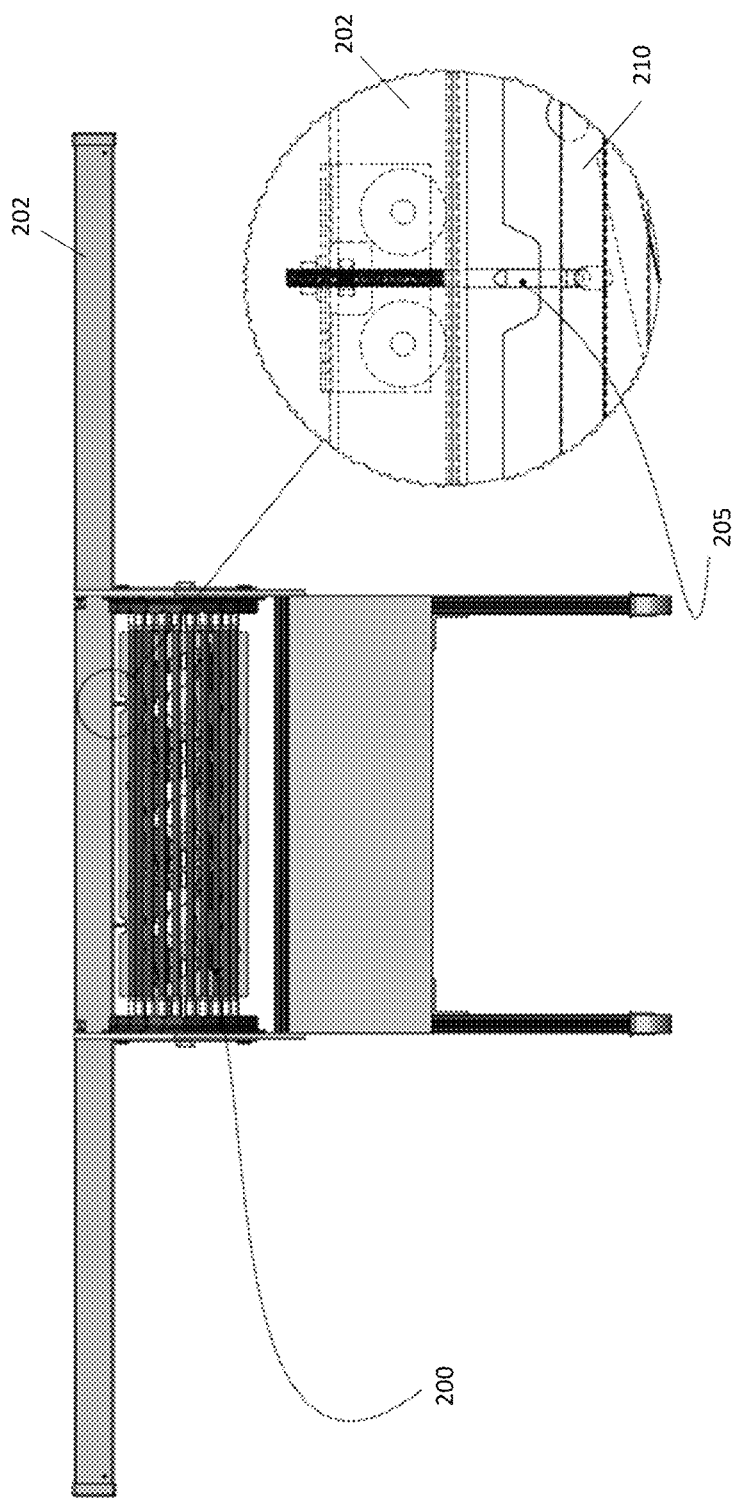
FIG. 2A depicts the disinfection system with the mask chamber walls removed to depict the lamp arrays in accordance with an illustrative embodiment.

FIG. 2A depicts the disinfection system with the mask chamber walls removed to depict the lamp arrays 200 in accordance with an illustrative embodiment. In FIG. 2A, the mask cassette is within the mask chamber for disinfection. FIG. 2A also includes an inset depicting a cross-sectional view of a cassette trolley rail 202. The inset shows that cassette hook(s) 205 and a mask cassette 210 are fully exposed to the UV disinfecting light emitted by the lamp arrays 200.

Figure 2B:
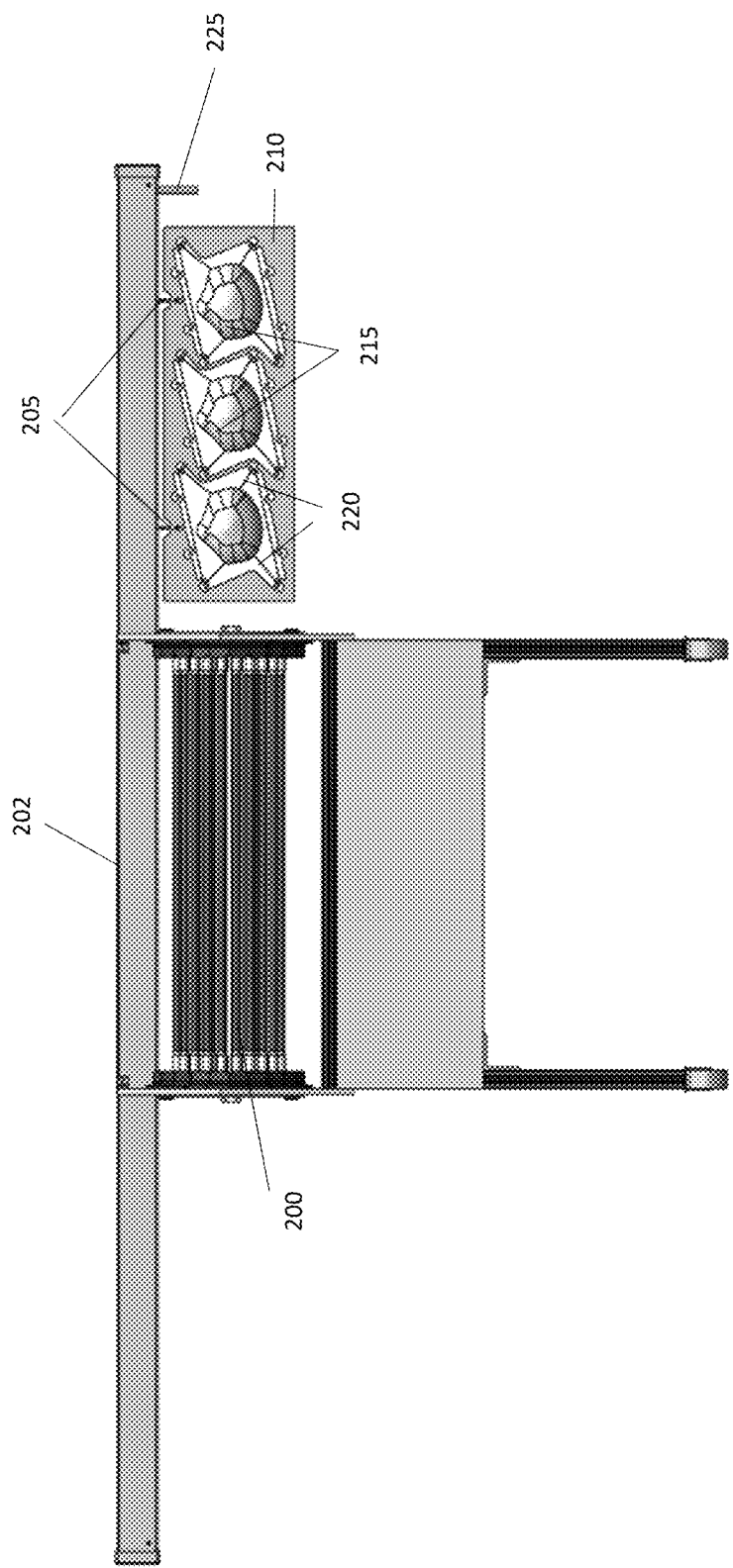
FIG. 2B depicts the disinfection system with the mask chamber walls removed and with the mask cassette in the clean position in accordance with an illustrative embodiment.

FIG. 2B depicts the disinfection system with the mask chamber walls removed and with the mask cassette 210 in the clean position in accordance with an illustrative embodiment. The masks are placed into the clean position after processing within the mask chamber, which can be for 1 minute in some embodiments. The masks 215, mask straps 220, mask cassette 210, trolley hooks 205, and trolley handle(s)225 are all disinfected within the mask chamber. As such, the mask cassette 210 can be removed from the cassette trolley rail 202, and the masks 215 can be removed therefrom and packaged for further use.

In certain embodiments described herein, the lamp arrays 200 mounted within the mask chamber include a first array of 10 lamps mounted to a first lamp mount and a second array of 6 lamps mounted to a second lamp mount. As shown, the first and second lamp mounts form curved (i.e., c-shaped) lamp array paths. The first array is positioned over an outer surface of the masks and the second array is positioned over an inner surface of the masks. As such, the first array can have a radius of curvature that differs from that of the second array to account for the different shapes found on the interior/exterior sides of the masks. In an illustrative embodiment, the curvature of the first and second lamp mounts can each be specific to the mask style that is being disinfected such that complete exposure of the mask is achieved. In alternative embodiments, different numbers of lamps and/or shapes of lamp array paths may be used for either of the lamp arrays.

Figure 3D:
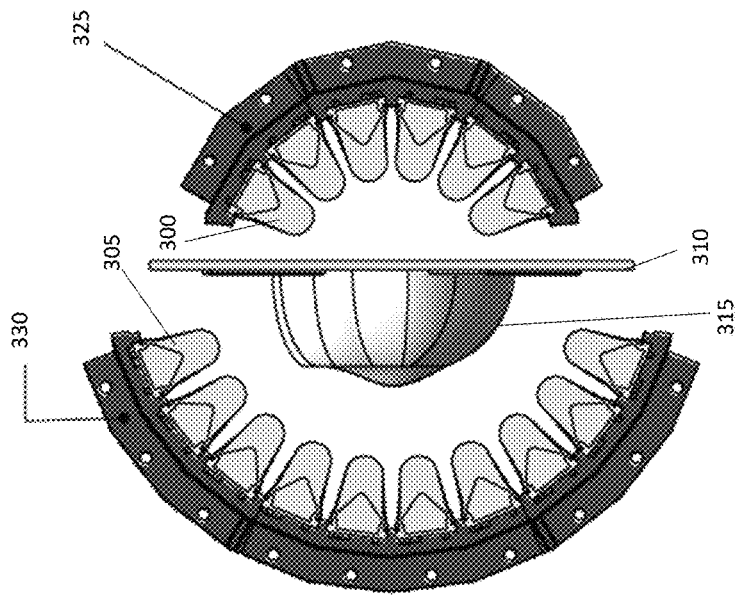
FIG. 3D is an end view of the lamp arrays with the mask cassette and masks therebetween in accordance with an illustrative embodiment.
Figure 3C:
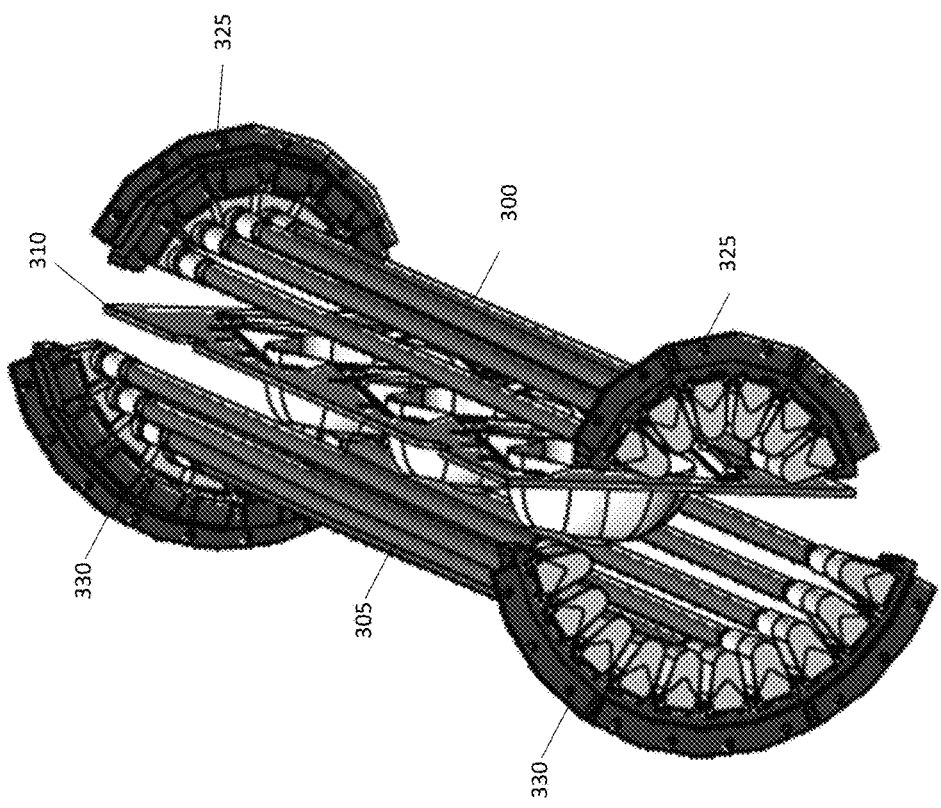
FIG. 3C is a perspective end view of the lamp arrays in accordance with an illustrative embodiment.
Figure 3E:
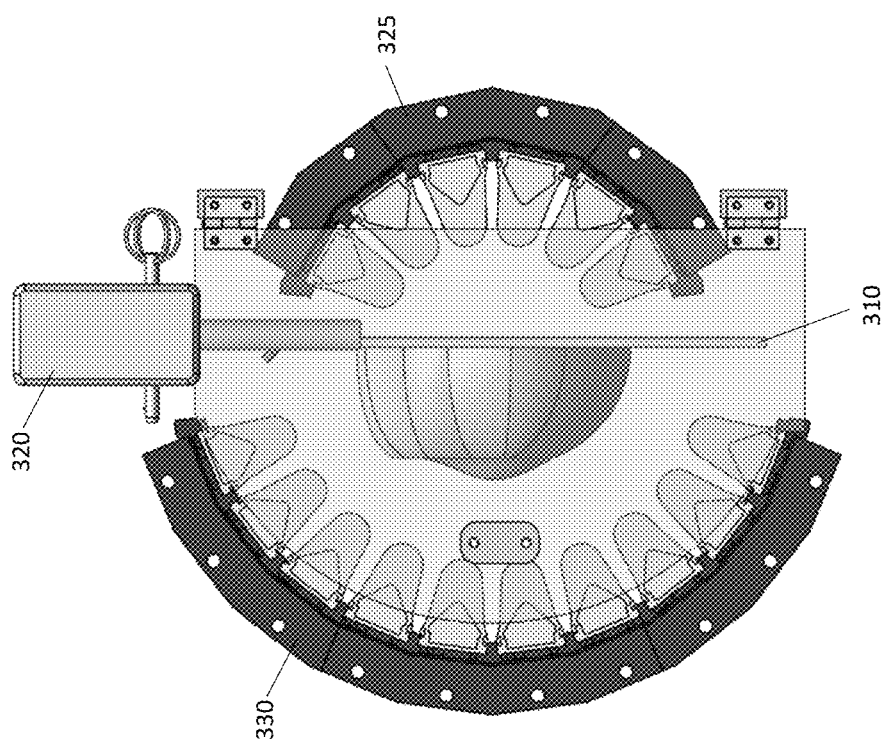
FIG. 3E is an end view of the lamp arrays, mask cassette (with masks), and cassette trolley rail in accordance with an illustrative embodiment.

FIG. 3A is a top view of a first lamp array 300 and a second lamp array 305 with a mask cassette 310 and masks 315 positioned between the lamp arrays in accordance with an illustrative embodiment. FIG. 3B is a side view of the lamp arrays in accordance with an illustrative embodiment. FIG. 3C is a perspective end view of the lamp arrays in accordance with an illustrative embodiment. FIG. 3D is an end view of the lamp arrays with the mask cassette 310 and masks 315 therebetween in accordance with an illustrative embodiment. FIG. 3E is an end view of the lamp arrays, mask cassette 310 (with masks 315), and cassette trolley rail 320 in accordance with an illustrative embodiment. The first lamp array 300 can be used to irradiate the inside of the masks, and the second lamp array 305 can be used to irradiate the outside of the masks.

As shown, the lamps and ballasts of each array are mounted to a lamp mount. Specifically, lamps of the first lamp array 300 are mounted to a first lamp mount 325 and lamps of the second lamp array 305 are mounted to a second lamp mount 330. In an illustrative embodiment, each of the lamp mounts 325 and 330 can include two pieces (one for each end of the lamps) that have the same curvature. Alternatively, each lamp mount can be a single, integral component that extends the entire length of the lamps. The lamp mounts can be made via 3D-printing, injection molding, or any other technique.

Figure 4B:
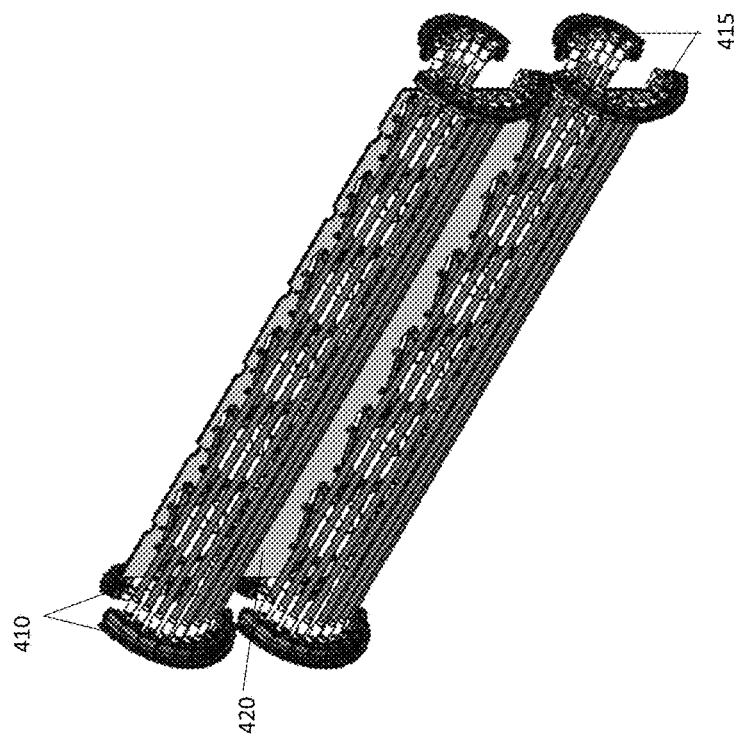
FIG. 4B is a perspective view of a double set of lamp arrays for use in a system with increased throughput in accordance with an illustrative embodiment.
Figure 4A:
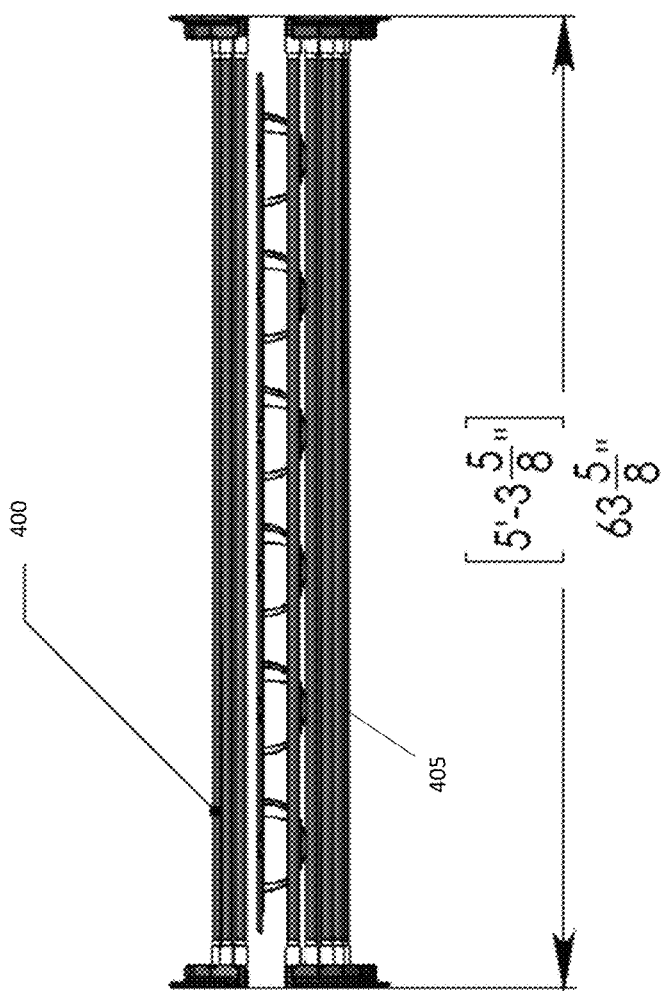
FIG. 4A depicts lamp arrays for an increased throughput system in accordance with another illustrative embodiment.

FIG. 4A depicts lamp arrays for an increased throughput system in accordance with another illustrative embodiment. In one embodiment, a first lamp array 400 and a second lamp array 405 of FIG. 4A are 63⅝ inches in length, which is double the length of those depicted in FIG. 3. As a result, the lamp arrays can disinfect twice as many masks at a given time, as compared to the shorter arrays. The bulbs of the lamp arrays can be Philips TUV64T5HO lamps with a UVC output of 422 microWatts/cm$^2$ at 1 meter. In alternative embodiments, other lamp array lengths and/or types of bulbs may be used.

Figure 4D:
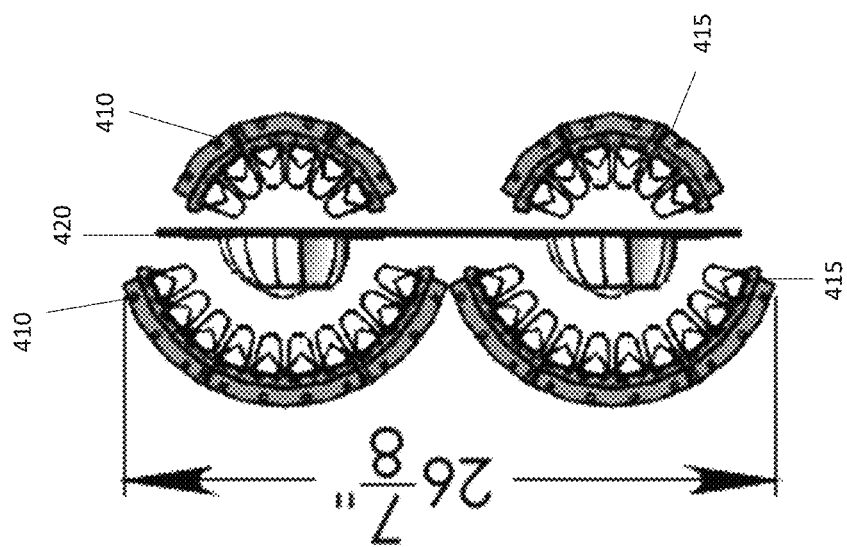
FIG. 4D is an end view of the double set of lamp arrays in accordance with an illustrative embodiment.
Figure 4C:
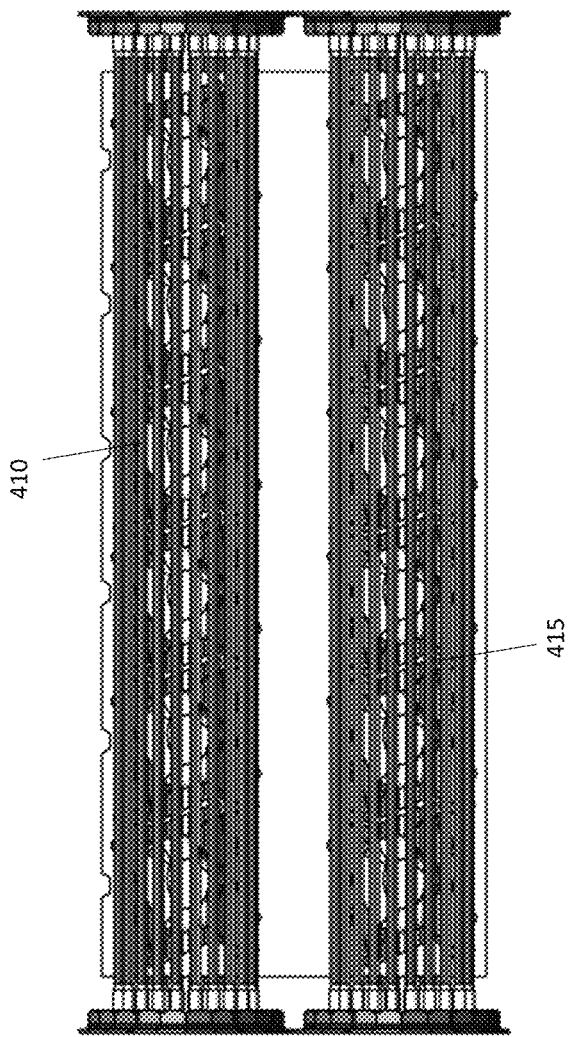
FIG. 4C is a side view of the double set of lamp arrays in accordance with an illustrative embodiment.

FIG. 4B is a perspective view of a double set of lamp arrays for use in a system with increased throughput in accordance with an illustrative embodiment. FIG. 4C is a side view of the double set of lamp arrays in accordance with an illustrative embodiment. FIG. 4D is an end view of the double set of lamp arrays in accordance with an illustrative embodiment. As shown, a first set of lamp arrays 410 is positioned one on top of a second set of lamp arrays 415 such that an extended mask cassette 420 having two rows of vertically oriented masks can be used. In one embodiment, an overall height of the double set of arrays is 26⅞ inches. In alternative embodiments, a different overall height may be used by using different sizes of the sets of lamp arrays. Additionally, the multiple sets of arrays can be mounted in another configuration, such as side by side. In another alternative embodiment, the multiple sets of arrays can instead be a vertically stacked triple set of arrays, quadruple set of arrays, etc. to further increase the system throughput. As discussed in more detail below, system throughput can further be increased by using higher power radiation, which reduces the amount of time that it takes for the masks to be disinfected.

Figure 5B:
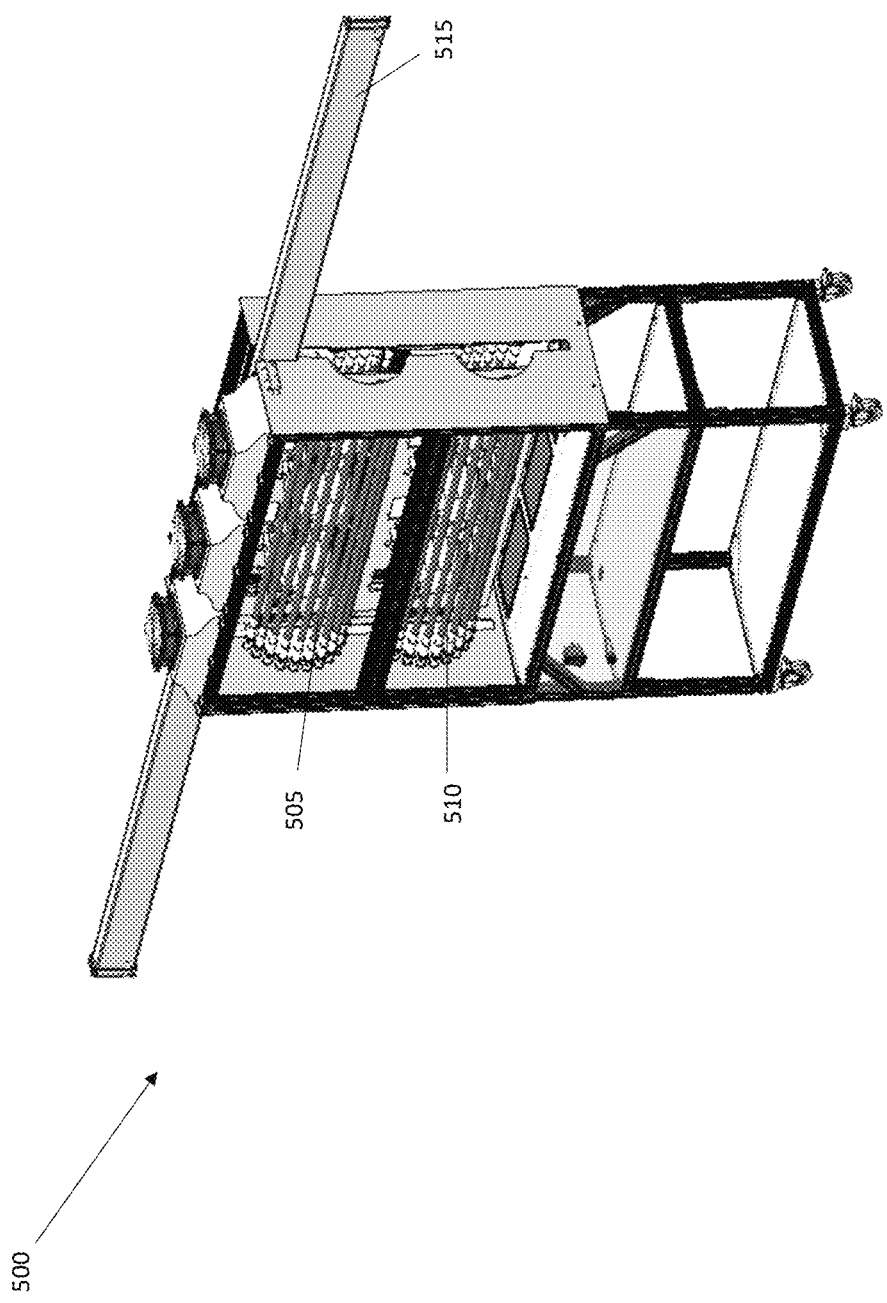
FIG. 5B is a second perspective view of the disinfection system of FIG. 5A in accordance with an illustrative embodiment.

FIG. 5A is a first perspective view of a disinfection system 500 with the mask chamber walls removed in accordance with another illustrative embodiment. FIG. 5B is a second perspective view of the disinfection system 500 of FIG. 5A in accordance with an illustrative embodiment. As shown, the disinfection system 500 includes a first set of lamp arrays 505 and a second set of lamp arrays 510 that are stacked vertically relative to one another. In alternative embodiments, a different relative positioning of the two sets of lamp arrays may be used. The disinfection system 500 also includes a cassette trolley rail 515 and a loaded mask cassette 520.

FIG. 5C is a perspective view of the lamp arrays, cassette trolley rail 515, and loaded mask cassette 520 in accordance with an illustrative embodiment. The embodiment of FIGS. 5A-5C uses a vertically stacked double set of lamp arrays for increased system throughput. In this embodiment, the lamp bases are custom designed to form curved lamp array paths corresponding to the front and back of the masks being disinfected. In an alternative embodiment, any of the lamp bases may be configured such that lamp array path is a straight line, instead of being curved.

Figure 5E:
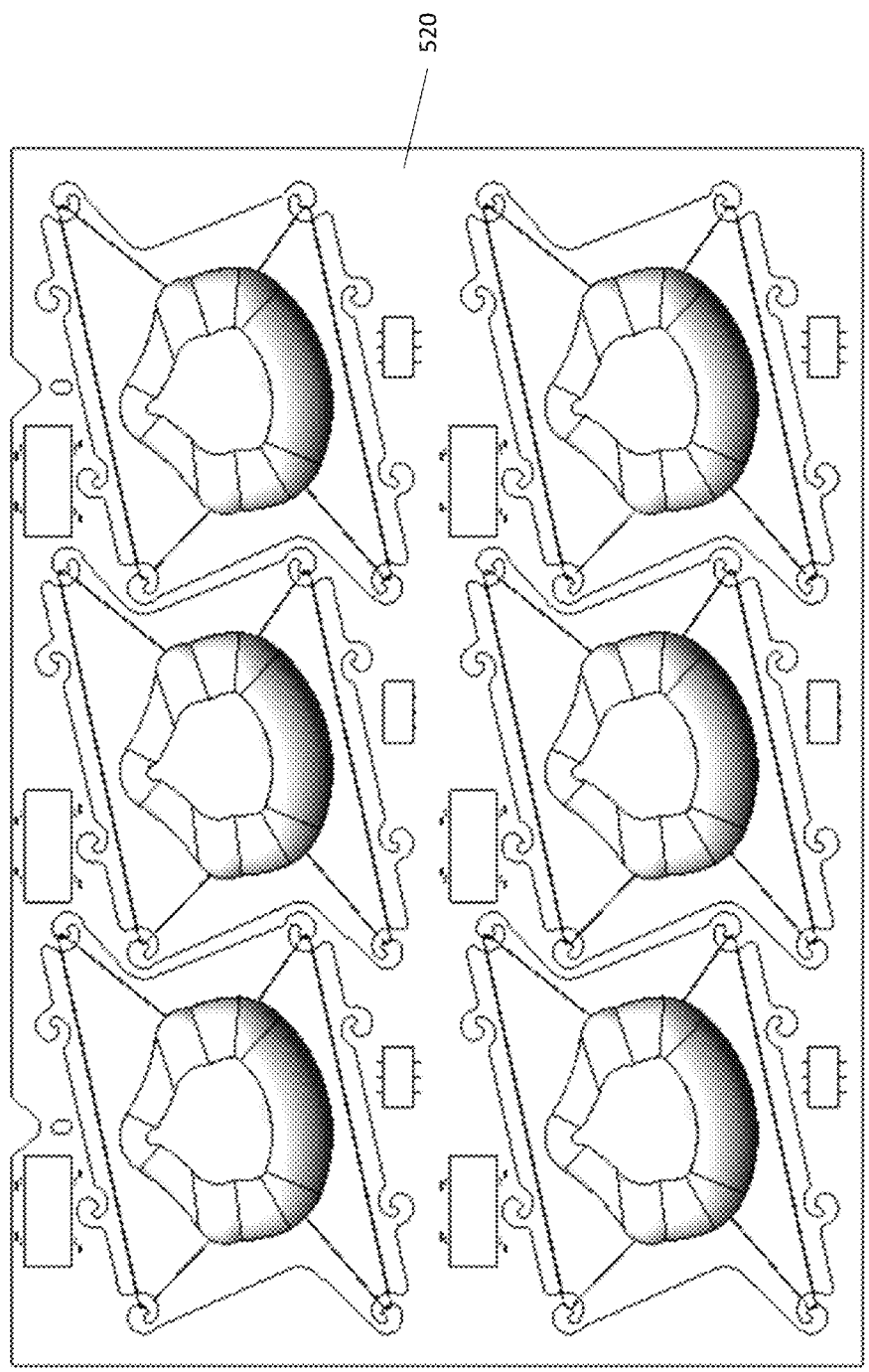
FIG. 5E depicts the loaded mask cassette from the embodiments of FIGS. 5A-5D in accordance with an illustrative embodiment.

FIG. 5D is an end view of the vertically stacked double set of lamp arrays in accordance with an illustrative embodiment. Also depicted in FIG. 5D is the cassette trolley rail 515 and the loaded mask cassette 520 mounted to the cassette trolley rail 515 such that the masks are in position to be disinfected by the lamp arrays. As also shown, the lamp array path of the lamps arrays positioned to emit radiation toward the outside of the masks has a fair amount of curvature, and is approximately c-shaped. The lamp array path of the lamp arrays positioned to emit radiation toward the inside of the masks has a small amount of curvature (i.e., a slightly curved line). In alternative embodiments, different lamp array paths may be used such as v-shaped, s-shaped, sawtooth, straight line, etc. depending on the type of masks (or other equipment) being disinfected. FIG. 5E depicts the loaded mask cassette 520 from the embodiments of FIGS. 5A-5D in accordance with an illustrative embodiment. In alternative embodiments, the loaded mask cassette 520 may be configured to hold fewer or additional masks.

Figure 6D:
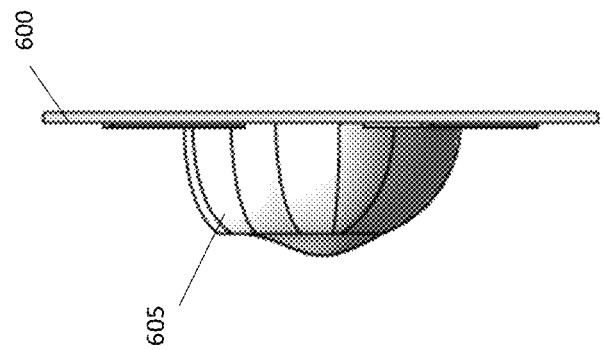
FIG. 6D is an end view of the mask cassette loaded with masks in accordance with an illustrative embodiment.
Figure 6C:
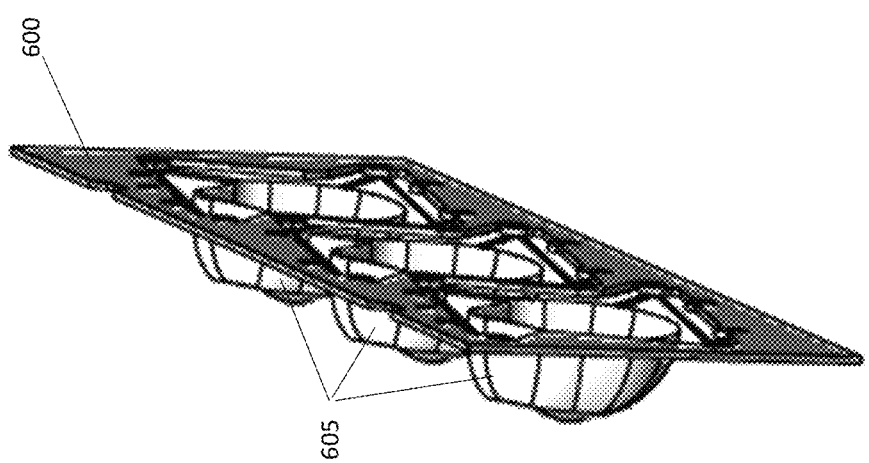
FIG. 6C is a perspective end view of the mask cassette loaded with masks in accordance with an illustrative embodiment.

FIG. 6A is a side view of a mask cassette 600 loaded with masks 605 in accordance with an illustrative embodiment. FIG. 6B is a top view of the mask cassette 600 loaded with masks 605 in accordance with an illustrative embodiment. FIG. 6C is a perspective end view of the mask cassette 600 loaded with masks 605 in accordance with an illustrative embodiment. FIG. 6D is an end view of the mask cassette 600 loaded with masks 605 in accordance with an illustrative embodiment. As shown, the mask cassette 600 includes three openings designed to accommodate three masks. In alternative embodiments, the mask cassette can be designed to hold additional or fewer masks. Each of the openings in the mask cassette includes a series of hooks 610 that are designed to secure the strap(s) 615 of the mask. The hooks 610 thus hold the masks in place (via the straps) and ensure that the straps are extended and fully exposed to the radiation. The mask cassette 600 can be formed via laser cutting, injection molding, or another technique. In any of the embodiments described herein, the mask cassettes can be made from acrylic, another plastic, metal, glass, etc.

A proof-of-concept prototype of the proposed system was constructed and has been used to test the throughput and effectiveness of the concept. The prototype has a decontamination rate of 4,000 masks per day. As discussed herein, alternative embodiments can be scaled up to process 32,000 or more masks per day. Using the prototype, initial validation studies show that germicidal irradiation is achieved at all mask surfaces in under a minute. Further, it has been found that the filtration characteristics of the mask are unchanged by application of the UV-C irradiation.

To help inform the theoretical design of the system, computational modeling of irradiation patterns based on a 3M™ model 1860 N95 respirator was performed in a medical physics lab. Underlying physical principles were used to determine the optimal irradiation pattern. Specifically, the inverse-square law of decreased irradiation with distance implies that the UV sources should be as close to the mask surface as feasible, without interfering with the transport of the masks through the system. Also, the "obliquity effect" or cosine law of irradiation field density implies that the beam source geometry should be optimized to the geometrical surface of the masks. Additionally, the effect of shadowing (i.e., occlusion by mask or container structures) was analyzed using multi-dimensional modeling to ensure that all surfaces of the masks were illuminated.

Based on the modeling results, an optimal UV lamp configuration was identified. The configuration includes two curved lamp arrays, one larger to illuminate the outward-facing surface of the mask and one smaller to illuminate the side of the mask that contacts the wearer's face. The length of the lamps relative to the spacing of masks in the array was a crucial parameter since the lateral surfaces of the mask are at risk of under-illumination if lamp lengths are too short.

The modeling results were used to design and build the proof-of-concept prototype device. Principles that drove the design of the prototype device included: 1) achieving complete decontamination of all N95 respirators processed, 2) providing sufficient throughput to meet the daily need of a hospital system, 3) maintaining decontamination of the N95 masks after processing, 4) maintaining mask integrity with respect to fit and filtration, 5) maintaining a safe environment for workers running the device, 6) providing a mechanism to maintain mask ownership during the disinfection process without marking the mask surface, 7) using standard manufacturing practices, and 8) providing internal validation measurements for every cycle of processing. All of these goals were met with the prototype design, which is described in more detail below.

Elements of the device include a mask chamber in which the UV lamp arrays sit, a cassette trolley rail at the top of the mask chamber on which a mask cassette can roll through the chamber, the detachable mask cassette to hold the masks, internal monitoring sensors, and cooling fans with HEPA filters. Specifically, masks are fixed to the removable mask cassette that travels through the system on the cassette trolley rail from the contaminated (used) side to the decontaminated (clean) side. Various components of the device were fabricated using a combination of 3-dimensional printing and laser cutting. Other components, such as the UV-C lamps, driving ballasts, connectors, fans, and HEPA filters were purchased from commercial sources. In alternative embodiments, the device can include fewer, additional, and/or different components and/or the components can be made using other techniques, such as injection molding.

Once assembled, the prototype was tested. Ultraviolet irradiance measurements were made to ensure that all surfaces of a mask were exposed to a germicidal dose. An International Light Technologies Model ILT770-NB spectrophotometer was used to measure the UV-C dose delivered to multiple locations and angles that followed the curved surfaces of the masks throughout the core of the lamp array. Based on the irradiance data, the exposure time required for each location and angle to reach the germicidal dose of 1 J/cm2 was determined.

Figure 7:
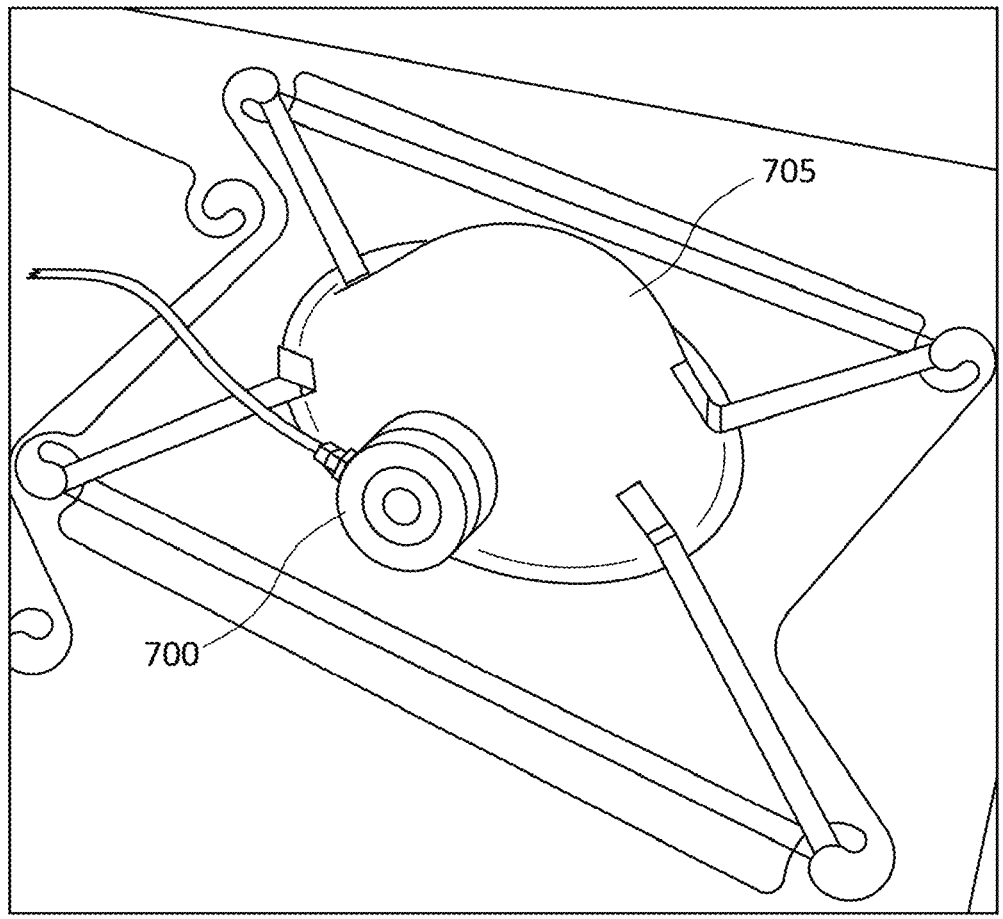
FIG. 7 shows an example configuration of a UV-C sensor mounted to a test mask in accordance with an illustrative embodiment.

FIG. 7 shows an example configuration of a UV-C sensor 700 mounted to a test mask 705 in accordance with an illustrative embodiment. The sensor 700 was positioned in five locations on the outside and five locations on the inside of the mask. FIG. 8 depicts a table that shows the results of measurements for the mask in the center of the array (Center) and a mask on the edge of the array (End) in accordance with an illustrative embodiment. From the table of FIG. 8 it can be seen that the sensor location "Side looking out" on an end mask had the lowest irradiance of 27 milliwatts/square centimeter (mW/cm$^2$). For this location to receive a germicidal dose of 1 J/cm$^2$, it would have to be exposed for 37 seconds. Thus, in one implementation, the illumination duration is set to 60 seconds, providing a safety factor 1.6 in attaining a germicidal dose of UV illumination on any mask surface. In alternative implementations for other mask models, the duration of exposure can be increased, with every additional 4 seconds representing a 10% increase in dose.

Figure 9:
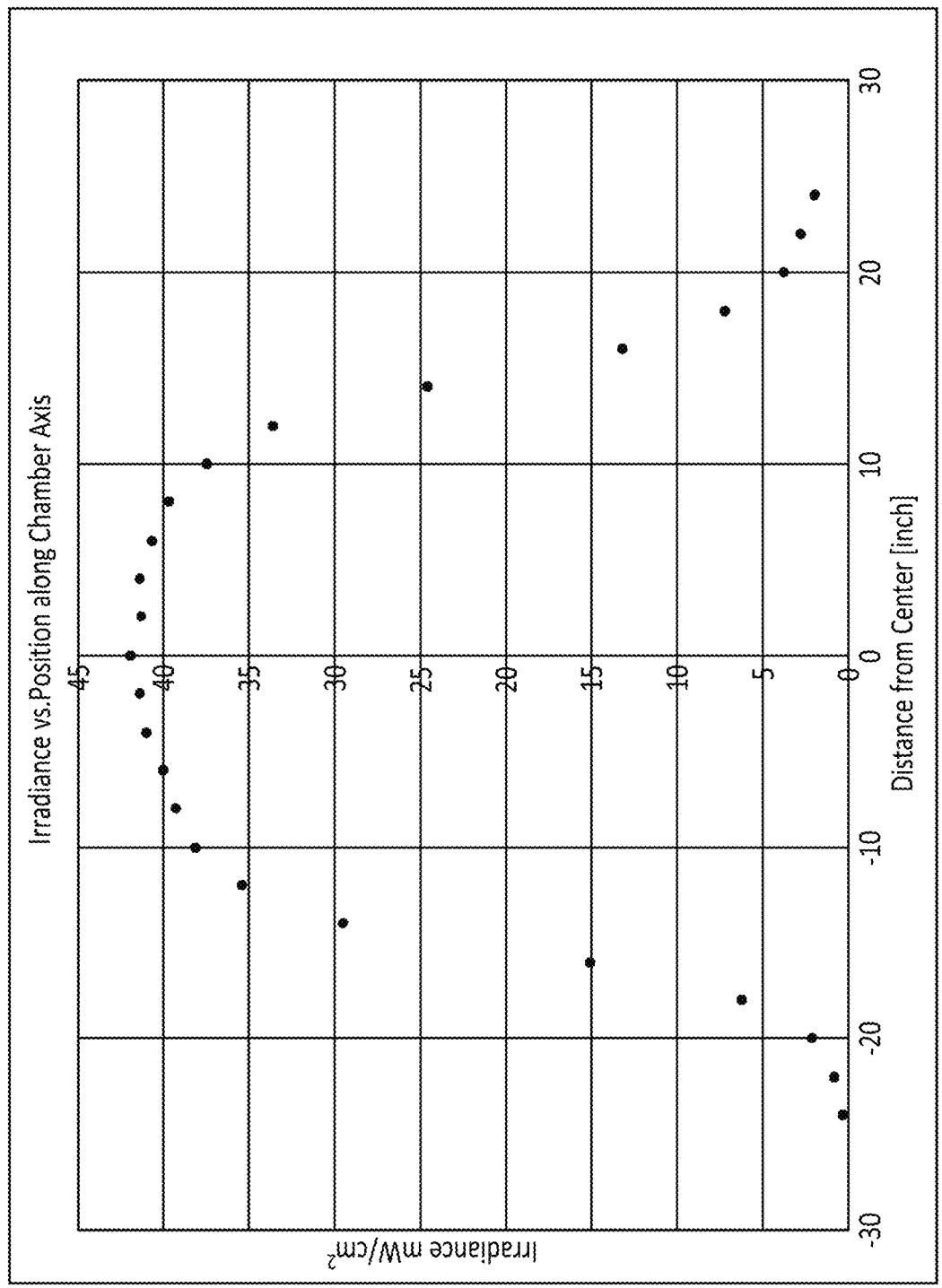
FIG. 9 depicts irradiance vs. position along an axis of the mask chamber in accordance with an illustrative embodiment.
Figure 10:
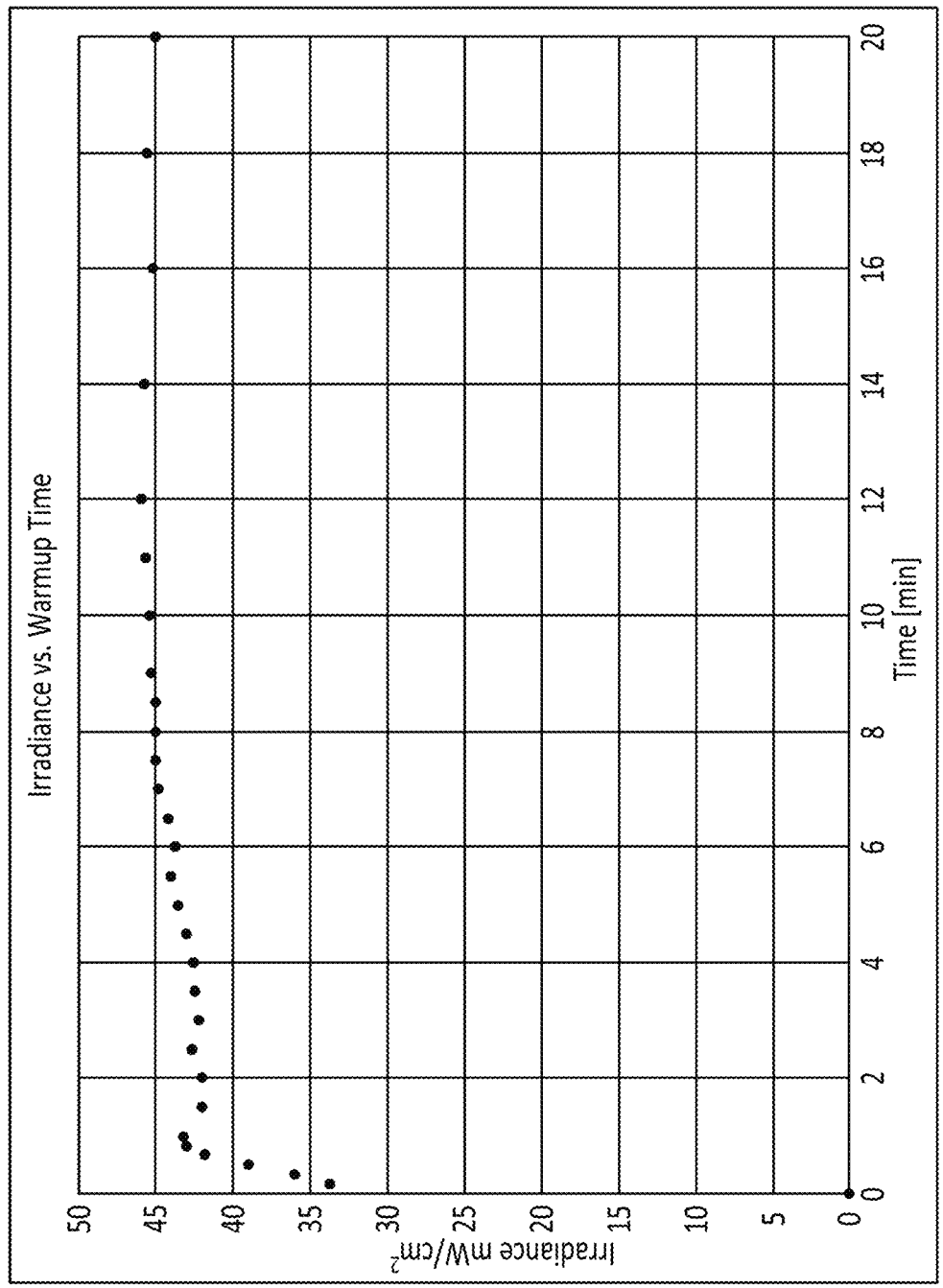
FIG. 10 depicts irradiance vs. warmup time for the lamps in accordance with an illustrative embodiment.
Figure 11:
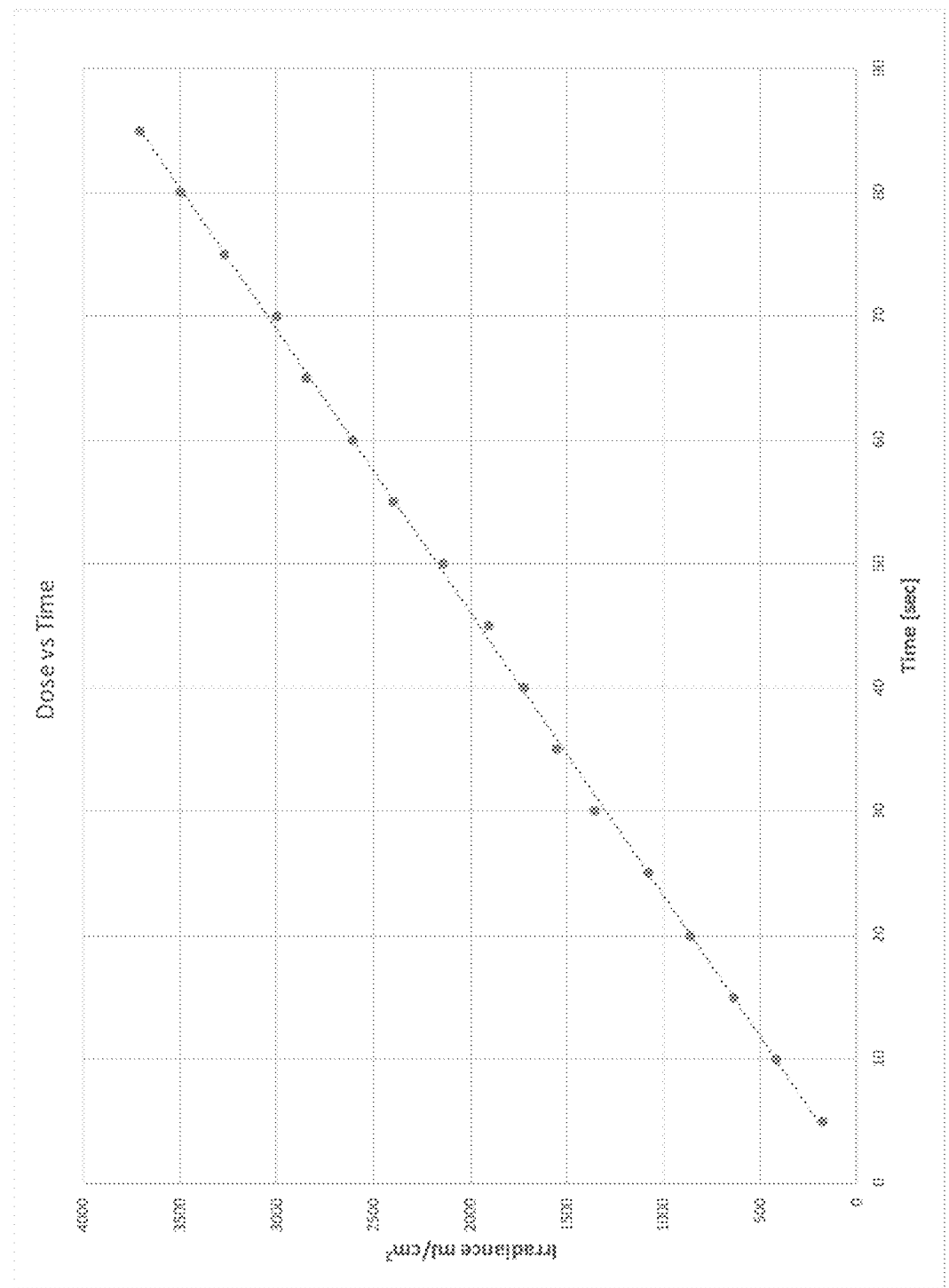
FIG. 11 depicts radiation dose vs. time for the decontamination system in accordance with an illustrative embodiment.
Figure 12:
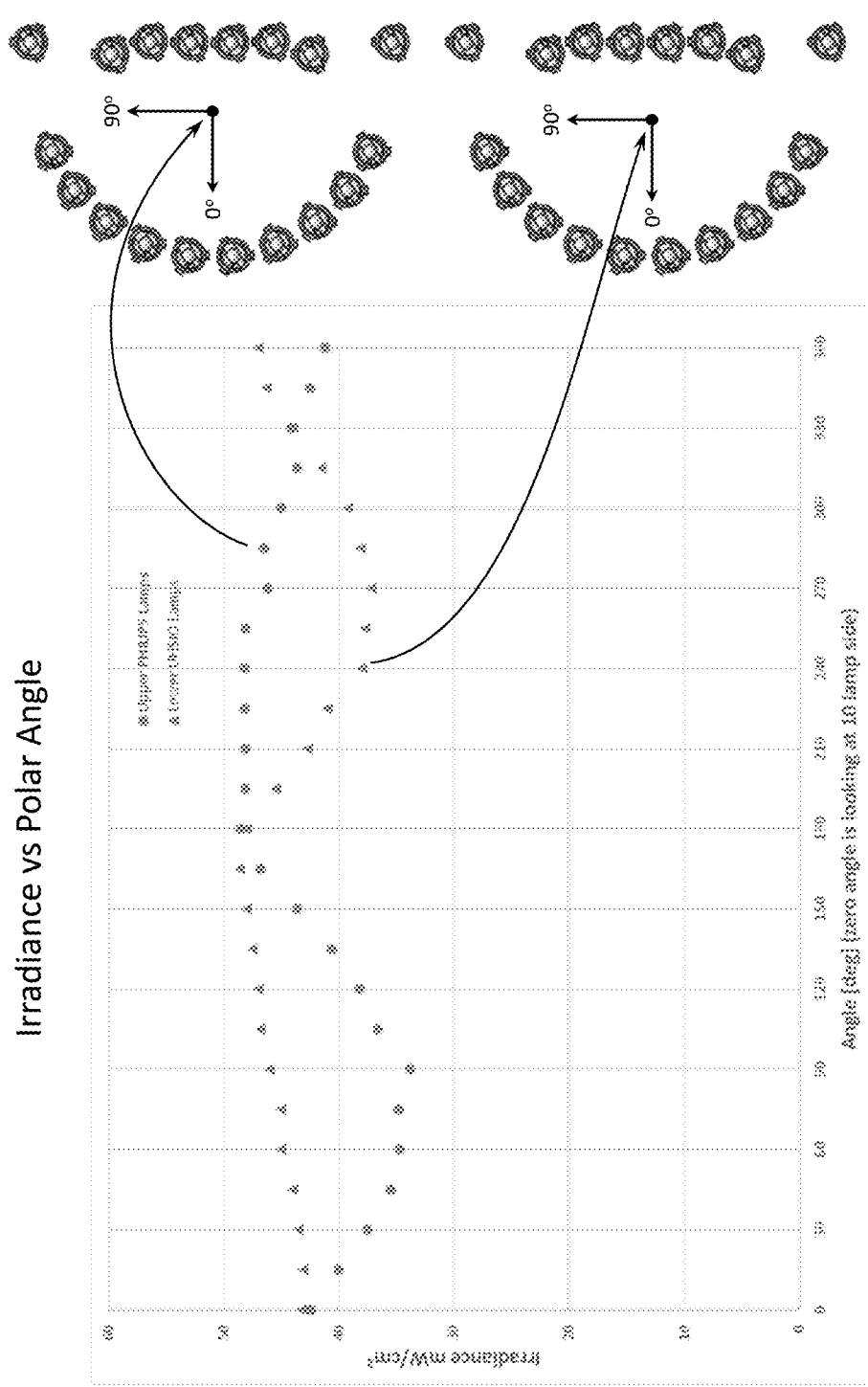
FIG. 12 depicts irradiance vs. polar angle in accordance with an illustrative embodiment.

Additional results of the testing and analysis are depicted in FIGS. 9-12. Specifically, FIG. 9 depicts irradiance vs. position along an axis of the mask chamber in accordance with an illustrative embodiment. FIG. 10 depicts irradiance vs. warmup time for the lamps in accordance with an illustrative embodiment. FIG. 11 depicts radiation dose vs. time for the decontamination system in accordance with an illustrative embodiment. FIG. 12 depicts irradiance vs. polar angle in accordance with an illustrative embodiment.

In summary, the testing and analysis showed that 2 minutes of decontamination is sufficient to reach 3-log reduction on all mask surfaces inoculated with *Escherichia coli* (*E. coli*) (i.e., front, back, strap(s), etc.). This 3-log reduction on the back surface of masks, which has not been demonstrated in other devices, reduces the risk of cross-contamination if the mask is inadvertently given to a different user. The testing also indicated that the back surface is the most difficult to decontaminate, likely due to its hydrophilicity. It is noted that the decontamination was tested with intact masks, and therefore accounts for both geometry (angle effect) and shadowing.

Post-decontamination fit of the masks is also an important consideration since poorly fitting masks are ineffective. Prior reports suggest the limiting factor in mask re-use will be the number of times a mask is donned and doffed rather than the UV decontamination process. Accordingly, it is possible that the mounting process onto the cassette could affect mask geometry and subsequent fit. Because the mask cassette can be readily manufactured from inexpensive materials, a variety of cassette designs can be made to accommodate different mask sizes, models, and strap tensions. The current cassette was designed to accommodate the 3M™ model 8210 N95 respirator without deformation or excess strain on straps. Post decontamination fit-testing can be conducted to certify other respirator models. Previous testing has further demonstrated that UVGI does not adversely affect filtration. For example, the 3M™ Company has tested several of their respirator models with UV-C 254 nm systems and found no adverse effects on respirator filtration or fit up to 100 J/cm$^2$ total cumulative dose.

Components of the device can be fabricated by 3-D printing in some embodiments. Injection molding can also be used to form device components more rapidly such that the device can be commercially produced. All other components of the device are commercially available or fabricated using standard techniques. The lamps used in the device have an average life of 1-2 years of continuous use, which minimizes maintenance time and costs. The device is also configured for electrical service in other countries through the use of ballasts with input voltage range of 120-277 Volts (V) at a frequency of 50 or 60 Hertz (Hz).

Masks that have been processed using the proposed system have provided a positive user experience. Unlike hydrogen peroxide based disinfection procedures, there was no irritation or residual chemical odor in the mask using the proposed system. This is key to tolerability and usability of the disinfected masks. In addition, feedback from end-users (nurses and physicians) has led to incorporation of a method for maintaining the identity of the owner of each mask, allowing the mask to be returned to the original user. Finally, the rapid decontamination cycle means that at the end of a shift, workers are able to receive their decontaminated mask before leaving the facility, which allows individuals to maintain control of their own PPE.

To ensure that sufficient illumination has occurred during each cycle, a UV-C irradiance sensor can be incorporated into the system (e.g., mounted inside the chamber). In the event that a lamp is lost during a cycle, the sensor can indicate an incomplete disinfection process. For example, the sensor can generate an alert (audio, visual, etc.) if it is determined that any of the lamps did not function for the entire disinfection cycle. The alert informs the operator that the masks may not be disinfected and should be run through the system again once the lamps are all functional.

Fans can also be installed in the system to keep the internal temperature of the chamber below 40° Celsius (C), which optimizes lamp performance and reduces the likelihood of a lamp burning out. An internal thermocouple can be used to monitor the temperature within the mask chamber, and the system can be configured to remove power to the lamps if the detected temperature exceeds a threshold temperature value of 50° C. Alternatively, a different threshold temperature value may be used. Ultraviolet irradiation of the air flowing through the chamber of the system, coupled with high-efficiency particulate air (HEPA) exit filters, prevents virus expulsion from the system, protecting workers and the external workspace. Importantly, the design of the system also provides a work-flow in which contaminated masks, cassettes, and cassette hooks are fully disinfected, eliminating the possibility of cross contamination. As discussed, contaminated materials enter one side of a chamber of the system and are removed, disinfected, on the opposite side of the chamber, providing complete separation.

Use of the proposed system is straightforward. To ensure safety, personal protective equipment can be used by workers putting respirators through the disinfection system. The PPE of the system operators can include masks, gloves, eye protection, and/or coveralls to provide protection from any virus that may be present on masks that are to be run through the system. Typical training time for use of the device is ~15 minutes.

The proposed system can also be scaled to meet the needs of different sizes and types of facilities. The proof-of-concept prototype that has already been built can disinfect enough masks (~4,000) in a day for a medium sized healthcare facility. However, larger facilities may wish to decontaminate a larger number of masks (e.g., 30,000 masks per day) to accommodate a larger work force. To scale up the device to process enough masks for large facilities the device can include UV-C lamps that are greater in length and/or that produce higher irradiance than the lamps used in the prototype. These lamps are currently manufactured commercially.

As an example, doubling the length of the lamps increases the capacity of the chamber by a factor of 2, and doubling the irradiance reduces the cycle time by a factor of 2 without affecting filtration or material strength. Because the geometries have been optimized in 3-dimensions, extending the lamp length does not alter the geometrical relationships, and all the validation studies from the proof-of-concept prototype hold for the proposed scaled-up device. Additionally, one or more additional sets of lamp arrays can be added to the system (e.g., above or below the original lamp arrays), which can double, triple, etc. the capacity. Together these modifications can increase the throughput by a factor of ~8 or more, allowing 32,000 or more masks to be disinfected in a day. For certain applications, it is desirable for the device to be narrow enough to permit passage through a standard doorway.

Thus, described herein is a high-throughput UV-based disinfection system for PPE such as N95 respirators and other face masks. The core of the system is an optimized arrangement of lamps designed using light-field modeling. The configuration provides full irradiation and disinfection of all respirator surfaces in under a minute. The system is segmented into contaminated and decontaminated compartments, and the masks are fixed to a removable cassette that travels through the system on a trolley.

In some embodiments, the disinfection system can be partially or fully automated and can include a computing system to control the automation. In such an embodiment, any of the operations described herein can be implemented in the form of computer-readable instructions that are stored on a tangible computer-readable medium and executable by a processing component. As an example, the system can utilize a computer that includes a memory which stores the computer-readable instructions, a processor which executes the stored computer-readable instructions, a transceiver that communicates with other computing devices, and an interface that allows a user to interact with and control the computer.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more."

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A disinfection system comprising:
    a mask chamber;
    a cassette trolley rail mounted to the mask chamber;
    a mask cassette configured to hold one or more masks and configured to mount to the cassette trolley rail such that the mask cassette translates along the cassette trolley rail;
    a first array of lamps mounted to a first lamp mount within the mask chamber, wherein the first array of lamps is positioned to emit radiation toward a first side of the mask cassette; and
    a second array of lamps mounted to a second lamp mount within the mask chamber, wherein the second array of lamps is positioned to emit radiation toward a second side of the mask cassette that is opposite the first side of the mask cassette.

2. The disinfection system of claim 1, wherein the cassette trolley rail includes a first portion that extends outside of the mask chamber at a used mask end of the mask chamber, a second portion that extends within the mask chamber, and a third portion that extends outside of the mask chamber at a clean mask end of the mask chamber.

3. The disinfection system of claim 2, further comprising a first cabinet positioned at the used mask end of the mask chamber and configured to house the first portion of the cassette trolley rail.

4. The disinfection system of claim 3, further comprising a second cabinet positioned at the clean mask end of the mask chamber and configured to house the third portion of the cassette trolley rail.

5. The disinfection system of claim 1, wherein the first lamp mount has a first radius of curvature and the second lamp mount has a second radius of curvature that is different than the first radius of curvature.

6. The disinfection system of claim 1, wherein the first array of lamps includes six lamps and the second array of lamps includes ten lamps.

7. The disinfection system of claim 1, wherein the mask cassette includes a plurality of openings configured to accommodate a corresponding plurality of masks.

8. The disinfection system of claim 7, wherein each of the plurality of openings includes a plurality of hooks configured to hold straps of the plurality of masks.

9. The disinfection system of claim 1, further comprising:
    a fan mounted to an opening in the mask chamber to provide air flow over the first array of lamps and the second array of lamps; and
    a filter mounted over the opening.

10. The disinfection system of claim 1, further comprising one or more hooks extending from the cassette trolley rail and configured to hold the mask cassette, wherein the one or more hooks are exposed to one or more of the first array of lamps and the second array of lamps during use of the system.

11. The disinfection system of claim 1, further comprising a thermocouple within the mask chamber to monitor an internal temperature of the mask chamber.

12. The disinfection system of claim 11, wherein the first array of lamps and the second array of lamps are configured to turn off if the internal temperature detected by the thermocouple exceeds a threshold value.

13. The disinfection system of claim 1, further comprising an irradiance sensor mounted within the mask chamber and configured to monitor the first array of lamps and the second array of lamps during a disinfection operation to ensure that all of the lamps are functional.

14. The disinfection system of claim 13, wherein the irradiance sensor generates an alert if it is determined that any of the lamps is not functional during the disinfection operation.

15. The disinfection system of claim 1, wherein each lamp of the first and second array of lamps extends along the same direction as the cassette trolley rail.

16. The disinfection system of claim 15, wherein each lamp of the first and second array of lamps is longer than a distance between most distant masks on a filled mask cassette.

* * * * *